US011589790B2

(12) United States Patent
Constandinou et al.

(10) Patent No.: US 11,589,790 B2
(45) Date of Patent: Feb. 28, 2023

(54) IMPLANTABLE NEURAL INTERFACE

(71) Applicant: Imperial College Innovations Limited, London (GB)

(72) Inventors: Timothy Constandinou, London (GB); Andrew Jackson, Newcastle-upon-Tyne (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 1134 days.

(21) Appl. No.: 16/301,748

(22) PCT Filed: May 19, 2017

(86) PCT No.: PCT/GB2017/051417
§ 371 (c)(1),
(2) Date: Nov. 15, 2018

(87) PCT Pub. No.: WO2017/199052
PCT Pub. Date: Nov. 23, 2017

(65) Prior Publication Data
US 2020/0315477 A1    Oct. 8, 2020
US 2021/0059547 A2    Mar. 4, 2021

(30) Foreign Application Priority Data

May 20, 2016    (GB) ...................... 1608958

(51) Int. Cl.
*A61B 5/24*       (2021.01)
*H04W 4/80*       (2018.01)
(Continued)

(52) U.S. Cl.
CPC ............... *A61B 5/24* (2021.01); *A61B 5/291* (2021.01); *A61B 5/6868* (2013.01);
(Continued)

(58) Field of Classification Search
CPC ......... A61B 5/24; A61B 5/291; A61B 5/6868; A61B 2560/0219; A61N 1/37229; H04W 4/80
See application file for complete search history.

(56) References Cited

U.S. PATENT DOCUMENTS

2006/0173259 A1* 8/2006 Flaherty ................... A61B 5/24
                                                          600/331
2007/0293908 A1* 12/2007 Cowan ................. A61N 1/0534
                                                          607/45
(Continued)

FOREIGN PATENT DOCUMENTS

WO    2010042750    4/2010
WO    2016030822    3/2016
WO    2016053375    4/2016

OTHER PUBLICATIONS

United Kingdom Search Report in corresponding UK appl. No. GB1608958.3, dated Nov. 18, 2016.
(Continued)

*Primary Examiner* — Christopher A Flory
(74) *Attorney, Agent, or Firm* — Kirschstein, Israel, Schiffmiller & Pieroni, P.C.

(57) ABSTRACT

A neural interface arrangement has multiple probes for subdural implantation into or onto a human brain. Each probe has at least one sensing electrode, a coil for receiving power via inductive coupling, signal processing circuitry coupled to the electrode(s), and a transmitter for wirelessly transmitting data signals arising from the electrode(s). An array of coils is implanted above the dura beneath the skull, for inductively coupling with the coil of each probe, and for transmitting power to the probes. A primary coil is connected to the coil array, for inductively coupling with an external transmitter device, and for receiving power from the external transmitter device. In use, the primary coil is
(Continued)

operable to receive power from the external transmitter device by inductive coupling and to cause the coil array to transmit power to the probes by inductive coupling, and the probes wirelessly transmit data signals arising from the electrodes.

20 Claims, 7 Drawing Sheets

(51) Int. Cl.
    *A61B 5/00* (2006.01)
    *A61B 5/291* (2021.01)
    *A61N 1/372* (2006.01)

(52) U.S. Cl.
    CPC .......... *A61N 1/37229* (2013.01); *H04W 4/80* (2018.02); *A61B 2560/0219* (2013.01)

(56) References Cited

U.S. PATENT DOCUMENTS

| | | |
|---|---|---|
| 2008/0021525 A1 | 1/2008 | Solzbacher et al. |
| 2009/0105784 A1 | 4/2009 | Massoud-Ansari |
| 2010/0262208 A1 | 10/2010 | Parker |
| 2011/0307079 A1* | 12/2011 | Oweiss ................ A61B 5/4094 600/545 |
| 2012/0184837 A1 | 7/2012 | Martens |
| 2012/0238855 A1* | 9/2012 | Lanning ................ A61B 5/0017 600/378 |
| 2012/0277834 A1* | 11/2012 | Mercanzini ........ A61N 1/36125 607/116 |
| 2012/0296444 A1* | 11/2012 | Greenberg ........... A61N 1/0531 607/152 |
| 2012/0302856 A1* | 11/2012 | Chang .................... A61B 5/291 600/378 |
| 2012/0310067 A1 | 12/2012 | Najafi |
| 2015/0157862 A1 | 6/2015 | Greenberg |
| 2016/0128589 A1 | 5/2016 | Tabib-Azar |
| 2016/0199656 A1* | 7/2016 | Phillips .............. A61N 1/36103 607/45 |
| 2016/0331968 A1* | 11/2016 | Greenberg ......... A61N 1/36046 |
| 2016/0367836 A1* | 12/2016 | Kampasi .............. G02B 6/0008 |

OTHER PUBLICATIONS

International Search Report in corresponding international appl. No. PCT/GB2017/051417, dated Jul. 26, 2017.
Written Opinion in corresponding international appl. No. PCT/GB2017/051417, dated Aug. 23, 2018.
Bansal, A. K., Truccolo, W., Vargas-Irwin, C. E., & Donoghue, J. P., "Decoding 3D reach and grasp from hybrid signals in motor and premotor cortices: spikes, multiunit activity, and local field potentials", Journal of neurophysiology, 107(5), pp. 1337-1355 (2012).
Baranauskas, G., "What limits the performance of current invasive brain machine interfaces?", Frontiers in systems neuroscience, 8 (2014).
Buzsáki, G., Anastassiou, C. A., & Koch, C., "The origin of extracellular fields and currents—EEG, ECoG, LFP and spikes", Nature reviews neuroscience, 13(6), pp. 407-420 (2012).
Campbell, P. K., Jones, K. E., Huber, R. J., Horch, K. W., & Normann, R. A., "A silicon-based, three-dimensional neural interface: manufacturing processes for an intracortical electrode array", Biomedical Engineering, IEEE Transactions on, 38(8), pp. 758-768 (1991).
Chae, M. S., Yang, Z., Yuce, M. R., Hoang, L., & Liu, W., "A 128-channel 6 mW wireless neural recording IC with spike feature extraction and UWB transmitter", Neural Systems and Rehabilitation Engineering, IEEE Transactions on, 17(4), pp. 312-321(2009).
Flint, R. D., Wright, Z. A., Scheid, M. R., & Slutzky, M. W., "Long term, stable brain machine interface performance using local field potentials and multiunit spikes", Journal of neural engineering, 10(5), 056005 (2013).

Gibson, S., Judy, J. W., & Marković, D., "An FPGA-based platform for accelerated offline spike sorting", Journal of neuroscience methods, 215(1), pp. 1-11 (2013).
Hall, T. M., Nazarpour, K., & Jackson, A., "Real-time estimation and biofeedback of single-neuron firing rates using local field potentials", Nature communications, 5 (2014).
Hara, S. A., Kim, B. J., Kuo, J. T., Lee, C. D., Gutierrez, C. A., Hoang, T., . . . & Meng, E., "Perforated 2×2 Parylene sheath electrode array for chronic intracortical recording", In Neural Engineering (NER), 2013 6th International IEEE/EMBS Conference on, pp. 645-648, IEEE (Nov. 2013).
Harris, K. D., Henze, D. A., Csicsvari, J., Hirase, H., & Buzsáki, G., "Accuracy of tetrode spike separation as determined by simultaneous intracellular and extracellular measurements", Journal of neurophysiology, 84(1), pp. 401-414 (2000).
Harrison, R. R., & Charles, C., "A low-power low-noise CMOS amplifier for neural recording applications", Solid-State Circuits, IEEE Journal of, 38(6), pp. 958-965 (2003).
Hochberg LR, Bacher D, Jarosiewicz B, Masse NY, Simeral JD, Vogel J, Haddadin S, Liu J, Cash SS, van der Smagt P, Donoghue JP, "Reach and grasp by people with tetraplegia using a neurally controlled robotic arm", Nature, 485(7398):372-5 (May 2012).
Kahn, J. M., Katz, R. H., & Pister, K. S., "Next century challenges: mobile networking for 'Smart Dust'", In Proceedings of the 5th annual ACM/IEEE international conference on Mobile computing and networking, pp. 271-278, ACM (Aug. 1999).
Kiani, M., & Ghovanloo, M., "A 20-Mb/s pulse harmonic modulation transceiver for wideband near-field data transmission", Circuits and Systems II: Express Briefs, IEEE Transactions on, 60(7), pp. 382-386 (2013).
Kiani, M., & Ghovanloo, M., "A figure-of-merit for designing high-performance inductive power transmission links", Industrial Electronics, IEEE Transactions on, 60(11), pp. 5292-5305 (2013).
Kim, E. G., John, J. K., Tu, H., Zheng, Q., Loeb, J., Zhang, J., & Xu, Y., "A hybrid silicon-parylene neural probe with locally flexible regions", Sensors and Actuators B: Chemical, 195, pp. 16-422 (2014).
Jow, U. M., & Ghovanloo, M.,"Optimization of data coils in a multiband wireless link for neuroprosthetic implantable devices", Biomedical Circuits and Systems, IEEE Transactions on, 4(5), pp. 301-310 (2010).
Lee, Y., Bang, S., Lee, I., Kim, Y., Kim, G., Ghaed, M. H., . . . & Blaauw, D., "A Modular 1 mm Die-Stacked Sensing Platform With Low Power I C Inter-Die Communication and Multi-Modal Energy Harvesting", Solid-State Circuits, IEEE Journal of, 48(1), pp. 229-243 (2013).
Liu, T., Bihr, U., Anders, J., and Ortmanns, M. (2014). Liu, T., Bihr, U., Anders, J., & Ortmanns, M., "Performance evaluation of a low power optical wireless link for biomedical data transfer", In Circuits and Systems (ISCAS), 2014 IEEE International Symposium on, pp. 870-873, IEEE (Jun. 2014).
Lopez, C. M., Andrei, A., Mitra, S., Welkenhuysen, M., Eberle, W., Bartic, C., . . . & Gielen, G. G., "An implantable 455-active-electrode 52-channel CMOS neural probe", Solid-State Circuits, IEEE Journal of, 49(1), pp. 248-261 (2014).
Motoyoshi, M., "Through-silicon via (TSV)", Proceedings of the IEEE, 97(1), pp. 43-48 (2009).
Najafi, K., Wise, K. D., & Mochizuki, T., "A high-yield IC-compatible multichannel recording array", Electron Devices, IEEE Transactions on, 32(7), pp. 1206-1211 (1985).
Parker, J. L., U.S. Appl. No. 12/549,786, filed 2009.
Polikov, V. S., Tresco, P. A., & Reichert, W. M., "Response of brain tissue to chronically implanted neural electrodes", Journal of neuroscience methods, 148(1), pp. 1-18 (2005).
Quiroga, R. Q., Nadasdy, Z., & Ben-Shaul, Y., "Unsupervised spike detection and sorting with wavelets and superparamagnetic clustering", Neural computation, 16(8), pp. 1661-1687 (2004).
Saeidi, N., Schuettler, M., Demosthenous, A., & Donaldson, N., "Technology for integrated circuit micropackages for neural interfaces, based on gold-silicon wafer bonding", Journal of Micromechanics and Microengineering, 23(7), 075021 (2013).

(56) References Cited

OTHER PUBLICATIONS

Seo, D., Carmena, J. M., Rabaey, J. M., Maharbiz, M. M., & Alon, E., "Model validation of untethered, ultrasonic neural dust motes for cortical recording", Journal of neuroscience methods, 244, pp. 114-122 (2015).

Sohal, H. S., Jackson, A., Jackson, R., Clowry, G. J., Vassilevski, K., O'Neill, A., & Baker, S. N., "The sinusoidal probe: a new approach to improve electrode longevity", The chronic challenge—new vistas on long-term multisite contacts to the central nervous system (2015).

Stevenson, I. H., & Kording, K. P., "How advances in neural recording affect data analysis", Nature neuroscience, 14(2), pp. 139-142 (2011).

Todorova, S., Sadtler, P., Batista, A., Chase, S., & Ventura, V., "To sort or not to sort: the impact of spike-sorting on neural decoding performance", Journal of neural engineering, 11(5), 056005 (2014).

Velliste, M., Perel, S., Spalding, M. C., Whitford, A. S., & Schwartz, A. B., "Cortical control of a prosthetic arm for self-feeding", Nature, 453(7198), pp. 1098-1101 (2008).

Viventi, J., Kim, D. H., Vigeland, L., Frechette, E. S., Blanco, J. A., Kim, Y. S., . . . & Wulsin, D. F., "Flexible, foldable, actively multiplexed, high-density electrode array for mapping brain activity in vivo", Nature neuroscience, 14(12), pp. 1599-1605 (2011).

Williams, I., Luan, S., Jackson, A., & Constandinou, T. G., "Live demonstration: A scalable 32-channel neural recording and real-time FPGA based spike sorting system", In Biomedical Circuits and Systems Conference (BioCAS), 2015 IEEE, pp. 1-5, IEEE (2015).

European Search Report in corresponding Divisional Application No. EP 20 19 9401, dated Dec. 8, 2020.

\* cited by examiner

IMPLANTABLE NEURAL INTERFACE

FIELD OF THE INVENTION

The present invention relates to a neural interface arrangement, for use in relaying electrical signals from the human brain to an external device or system. The present invention is particularly applicable, but by no means limited, to relaying signals for the purpose of effecting control of an external device. Other applications are also possible, such as taking an output from the sensory cortex. The present principles may also be used to provide stimulation to the brain.

BACKGROUND TO THE INVENTION

Being able to control devices with our thoughts (i.e. to provide a motor interface between the brain and an external device) is a concept that has long captured the imagination. Neural Interfaces or Brain Machine Interfaces (BMIs) are devices that aim to do precisely this. For more than half a century neuroscientists have recorded the characteristic action potentials (spikes) generated by cortical neurons in order to understand how information is represented and transmitted through the nervous system. Until recently, these experiments involved sampling small numbers of neurons over short sessions of a few hours, but with advances in microtechnology we can now record from hundreds of neurons over many weeks, months or even years. The fact that such technology has enabled us to transition from experimental work on rodents, to monkeys, to human applications, in such a short time is a testament to the scientific and neurotechnology communities. These efforts are now inspiring new translational efforts to develop such technology to communicate directly with the nervous system for therapeutic benefit. For example, neural signals from the motor cortex of paralysed patients have been used to operate assistive devices such as computers and robotic prostheses in respect of monkeys (Velliste, 2008) and humans (Hochberg, 2012). The impact of similar devices has already been demonstrated in sensory and cognitive prostheses, for example, cochlear implants for the deaf, and deep brain stimulation (DBS) therapy for Parkinson's disease and dystonia.

The present inventors have identified a number of shortcomings and other considerations in respect of existing BMI devices, as follows: Channel Count: The trend has been to increase the number (and density) of recording channels, by scaling electrodes and electronics through exploiting modern micro-technologies, inspired by Moore's law (Stevenson, 2011). Silicon probes such as Utah (Campbell, 1991) and Michigan probes (Najafi, 1985) are currently the workhorse in experimental labs using either off-the-shelf electronics, e.g. Intan Tech. (Harrison, 2003); custom integrated circuits, e.g. (Lopez, 2013); or benchtop/rack-mounted instrumentation. Despite this increasing number of recording channels, the increase in decoded information rate is not linear; in fact, this appears to be logarithmically proportional (Baranauskas, 2014). This means, that in order to achieve information quality that is sufficient for motor control, recording systems will require orders of magnitude more recording channels, i.e. 1000s. Such large numbers of channels are not achievable with pre-existing systems, for which the number of channels is limited to the order of 100.

Neural Signal Processing: There is currently an open debate as to which data to use for achieving the best decoding strategy (Todorova, 2014). For each channel, this can utilise data from: (1) the local field potential; (2) all detected spikes; (3) all sorted spikes; (4) selected sorted spikes (based on most 'relevant' neurons). It has been demonstrated that both spikes but also local field activity can be used to decode cortical activity (Bansal, 2012). Spike sorting is a process that is typically applied to recorded offline data to ascertain from which neuron each spike has originated. For each recording, this involves detecting when all the spikes occur, then for each spike extracting specific features which are then used to classify the spikes. To achieve good sensitivity (i.e. classification accuracy) is challenging and is often a laborious task requiring manual supervision. State-of-the-art unsupervised algorithms use expectation maximisation for correlated recordings, e.g. using tetrodes (Harris, 2000) or super-paramagnetic clustering (Quiroga, 2004) but are too complex to process in real-time for multiple channels. Recently, a number of hardware-efficient methods have been proposed (Gibson, 2013) (Williams, 2015) but these require training and/or user calibration to achieve good accuracy.

Stability of Extracellular Recordings: A key challenge in in-vivo recording of single unit activity has been to maintain stable (consistent and reliable) recordings chronically (over months and ideally years). Most often, it is observed that the single unit activity (i.e. spike waveforms) "fade" over a period of days to weeks until the spiking activity is indistinguishable from the noise. There are several underlying mechanisms for this, including tissue damage, gliosis (scar tissue growth), electrode movement, electrode degradation, etc. (Polikov, 2005) Given that the electrode needs to be in close proximity (up to 100-200 microns) to the neuron in order to clearly observe a signal, any microscopic changes in the local environment will affect the signal quality. Local field potentials, on the other hand, rely on a lower frequency signal that is generated by the local network activity (including several neurons spreading several hundreds of microns—e.g. 500 µm to 1 mm across) (Buzsaki, 2012) and as such are typically significantly more stable (than observing single unit activity) to microscopic changes. (Flint, 2013) Furthermore, it has recently been shown that local field potential recordings can be used to predict single unit activity, demonstrating that the same underlying information is present. (Hall, 2014)

Power and Communication: This poses a unique challenge for all active implanted devices, as it is highly undesirable to have any percutaneous connections (i.e. wires through the skin). All such devices thus have a transcutaneous link that typically utilises near-field (i.e. inductive) coupling for power delivery and data telemetry. Additionally, an implanted battery (either rechargeable or not) may be an option depending on the lifetime and power requirements of the device. In designing such a telemetry there are multiple conflicting trade-offs, for example, a low frequency carrier is often desirable for power transfer (to reduce EM absorption and avoid undesirable heating), but this opposes requirements for a high data rate communication. This remains a key challenge for emerging applications that require relatively high data rates such as retinal prosthetics (streaming images) and BMIs. There have been several proposed solutions in the literature, including novel modulation schemes (Kiani, 2013a), multi-coil inductive coupling (Kiani, 2013b), ultrawideband (Chae, 2009) and optical transmission (Liu, 2014).

Electrodes, Interconnects and Packaging: It is often due to mechanical failure/biocompatibility that implanted devices fail in chronic deployment and this therefore dictates the overall viability. Key challenges here include the integrity of packaging (hermeticity and biocompatibility), electrode stability (due to gliosis) and interconnect reliability (wires breaking).

Microelectrodes: The majority of high density penetrating probes are typically rigid, silicon-based (Campbell, 1991) (Najafi, 1985) with electrodes patterned using an inert metal (e.g. platinum, iridium). Although these are used extensively in experimental work and can provide excellent short term, highly localised recordings, their long-term stability in chronic experiments or for human use has proved challenging. This is in part due to mechanical issues: (1) tissue damage caused when implanting sharp, rigid probes implanted into a soft tissue; (2) electrodes will inevitably move/rub on tissue over time. This results in a build up of glial cells which 'encapsulates' the electrode, thus effectively screening the electrical signal. On the other hand, larger, non-penetrating electrodes that have been used more chronically tend to be on a soft, flexible substrate, e.g. cuff electrodes. Such electrodes have also started emerging for also intracortical applications, including a soft parylene sheath electrode (Hara, 2013), a hybrid partially flexible parylene/silicon probe (Kim, 2014), and a flexible 'sinusoidal' silicon probe (Sohal, 2014). Furthermore, there are new flexible thin/thick film and/or microelectronic technologies emerging that are being applied to, for example, electrocorticography (Viventi, 2011).

Packaging: Typical implantable devices (e.g. cochlear implants, DBS devices) utilise a cm-sized metal (typically titanium) can with ceramic/composite header for feedthroughs (i.e. interconnects) to achieve a hermetic seal with dry gas inside package (Yin, 2013). If mm-sized electronics (high field strength regions) are to be protected in the same way, then it is essential to make hermetic seals that are very small but also of proven reliability. Recent work is investigating using materials and fabrication processes used in semiconductor foundries to achieve chip-scale packaging. These utilise either a crystalline substrate (Parker, 2010) or the silicon substrate (with active microelectronics) itself with a low temperature sealant (i.e. CMOS compatible) (Saeidi, 2013). These micropackages are then coated in a biocompatible silicone or polymer. For example, Parylene C is biocompatible but also provides an excellent moisture barrier itself (compared to polymers). This requirement for hermeticity (low water transmission) is however incompatible with the desire for mechanical flexibility. There therefore exists a challenge on how to join the rigid package to flexible wires/tracks/electrodes.

Interconnects & Feedthroughs: In microsystems, connecting to the electrodes (and the required isolation/insulation) is achieved using several methods depending on technology: (1) for a planar substrate (e.g. CMOS, NeuroNexus), using buried conductors within insulating dielectrics; (2) for flexible electrodes, using a bespoke ribbon cable by patterning the conductors within an insulated polymer (e.g. silicone, polyamide, parylene); (3) wire/chip-to-chip, wire or bump bonding and encapsulation using polymer, epoxy or other resin. For integrated electrodes, new through-silicon-via (TSV) capabilities in CMOS are presenting exciting new opportunities (Motoyoshi, 2009). This involves typically etching a hole through the substrate, insulating using oxide growth and filling with a metal to create the TSV. A bondpad can then be positioned on the underside of the substrate, centred on this TSV with the appropriate isolation.

Distributed Neural Interfaces: The idea of 'smart dust' has been around for over a decade now (Kahn, 1999), proposing to create dust particle sized self-powered smart devices that interact with their surroundings. The challenge has largely been how to harvest sufficient energy within a minuscule volume and implement the entire system to do something useful. Recently, cubic mm-sized devices have been reported (Lee, 2013) towards this aim, however still without the 'killer' application having been achieved. The 'brain dust' concept (Seo, 2014) may be a step towards a distributed neural interface, targeting cubic-micron sized devices to interface to the brain. However, much of the effort thus far appears to be focused on the concept of ultrasonic power delivery.

SUMMARY OF THE INVENTION

According to a first aspect of the present invention there is provided a neural interface arrangement as defined in Claim 1 of the appended claims. Thus there is provided a neural interface arrangement comprising: a plurality of wireless probes for subdural implantation into or onto a human brain, each probe including at least one sensing electrode, a coil for receiving power via inductive coupling, signal processing circuitry coupled to the sensing electrode(s), and means for wirelessly transmitting data-carrying signals arising from the sensing electrode(s); an array of coils for implantation above the dura, beneath the skull, the array of coils being for inductively coupling with the coil of each of the plurality of probes, for transmitting power to the probes; and a primary (e.g. subcutaneous) coil connected to the array of coils, the primary coil being for inductively coupling with an external transmitter device, for receiving power from the external transmitter device; wherein, in use, the primary coil is operable to receive power from the external transmitter device by inductive coupling and to cause the array of coils to transmit power to the plurality of probes by inductive coupling; and wherein, in use, the plurality of probes are operable to wirelessly transmit data-carrying signals arising from the sensing electrodes.

By virtue of the use of two inductively-coupled links in this manner, one across the skin and the other across the dura, power can be conveyed efficiently and reliably from the external transceiver device to the probes, without the need for the probes to have any directly-connected power source such as an implanted battery, or associated interconnects.

Optional features are defined in the dependent claims.

In accordance with our presently-preferred embodiments, at least some of the probes include a plurality of discrete sensing electrodes, with each sensing electrode providing an independent reading (i.e. an independent recording channel). In such a manner, a number of recording channels may advantageously be obtained from a single probe, e.g. from different depth positions or different lateral positions on the probe.

At least some of the probes may be of drawing-pin-like form, having a head and a rigid shank, with the at least one sensing electrode being located on the shank. Such probes are relatively easy to push into the brain tissue. Furthermore, a plurality of sensing electrodes may advantageously be located at different depth positions along the shank.

Alternatively, or in addition, at least some of the probes may be without a shank, for surface recording (i.e. on the surface of the brain), the sensing electrode(s) being planar electrode(s).

Alternatively, or in addition, at least some of the probes may be of another drawing-pin-like form, having a head and a non-rigid shank, the shank being made up of a plurality of flexible and/or soft insulated wires, each wire being connected to a respective electrode. Such a probe is considered to cause less trauma to the brain tissue on insertion, and to be more likely to be accepted (rather than rejected) in the body. Again, a plurality of sensing electrodes may advantageously be located at different depth positions along the shank. In such probes having a non-rigid shank, the constituent wires may for example be linear and substantially parallel to one another, or may be arranged differently, for example in a braided manner.

In our presently-preferred embodiments, with each of the plurality of probes, the or each electrode is configured to sense the local electric field potential on or in the brain. In comparison to pre-existing techniques in which electrodes specifically record neuron activity, measurements of the local electric field potential have been found to remain stable for an extended period of time, and are less susceptible to degradation over time (e.g. due to scar tissue forming around the probe).

Preferably each of the plurality of probes further includes a reference electrode. A reference electrode may be located anywhere on a probe, such as at the surface end of the probe (which is advantageous for providing depth recording relative to a surface reference), or at the distal tip of a drawing-pin-like probe, for example.

In our presently-preferred embodiments, in each of the plurality of probes the signal processing circuitry is in the form of a complementary metal-oxide semiconductor (CMOS) system on a chip.

By way of example, in each of the plurality of probes, the signal processing circuitry may include a power management module and a communication module.

The power management module may include rectification circuitry and regulation circuitry.

The communication module may include downlink circuitry and uplink circuitry.

The downlink circuitry may be connected to configuration and control circuitry, for configuring and controlling the operation of the probe.

The uplink circuitry may be connected to processing and encoding circuitry, for processing and encoding signals arising from the probe's electrode(s).

Preferably, in the signal processing circuitry of each of the plurality of probes, the output of the or each sensing electrode is supplied to a respective low noise amplifier. Preferably the output of the reference electrode is also supplied to the or each low noise amplifier, such that the or each low noise amplifier subtracts the reference electrode signal from the respective sensing electrode signal.

Preferably, in the signal processing circuitry of each of the plurality of probes, the output of each low noise amplifier is provided to a multiplexer and buffer, preferably via a band-pass filter.

Further, in the signal processing circuitry of each of the plurality of probes, the output of the multiplexer and buffer is preferably provided to an analogue-to-digital converter, the output of which is then provided to the processing and encoding circuitry.

In our presently-preferred embodiments, in each of the plurality of probes, the electrode(s) are coupled to the signal processing circuitry by means of one or more through-silicon-vias. However, other approaches are also possible, such as using conductors that are "tunnelled" within inter metal dielectrics (IMDs) underneath a hermetic seal to the edge of the chip; or using an interposer layer.

Additionally, in our presently-preferred embodiments, in each of the plurality of probes, the signal processing circuitry is provided within micropackaging.

Preferably, each of the plurality of probes is passivated in a protective insulator.

Preferably, each of the plurality of probes is encapsulated in a biocompatible coating.

Preferably, in each of the plurality of probes, the coil comprises a millimetre-scale coil.

Preferably, in each of the plurality of probes, the coil is located in the head of the probe, i.e. close to the dura, and thus minimising the distance between said coil and said array of coils.

In one embodiment, the electrode(s) of the probes may be spring-biased into an extended position, and means provided for holding the electrode(s) in a retracted position prior to implantation. For example, a biodegradable or dissolvable coating (e.g. made of sugar) may be provided around the probe. In such a manner, once the probe has been implanted, the coating dissolves or degrades, enabling the electrodes to spring outwards, from the retracted position to the extended position. Outward extension of the electrodes in such a manner advantageously improves the retention of the electrodes in the brain tissue.

Turning now to the array of coils, particularly preferably the coils overlap with each other. This mitigates the issue of potential misalignment between the coils in the probes and the coils of the array.

Preferably, in the array of coils, the coils are millimetre-scale coils.

To facilitate introduction into the head, the array of coils is preferably embedded within a sheet (e.g. a silicone sheet).

Particularly preferably the neural interface arrangement further comprises a multiplexing chip connected between the array of coils and the primary coil. Preferably, each coil in the array is independently connected to the multiplexing chip.

To facilitate introduction into the patient's head, the array of coils, the multiplexing chip and the primary coil may all be integrated within a device of unitary form (e.g. coated in a flexible encapsulant). When a section of the patient's skull is removed to enable the probes to be implanted, such a device may be readily fitted around the removed section of skull (or an artificial replacement therefor, e.g. made by 3D printing), with the array of coils on the underside of the skull section and the primary coil on the outside of the skull section. The section of the skull (or artificial replacement therefor) may then be re-fitted to the patient's head, with the array of coils, the multiplexing chip and the primary coil all in place.

Alternatively, the primary coil may be provided as a separate entity from the array of coils, thereby enabling the primary coil to be located elsewhere on the scalp, or anywhere on the head, or indeed anywhere on the patient's body (e.g. on their chest).

With respect to the wireless transmission of data-carrying signals arising from the sensing electrodes, this may be done in a number of ways. In our presently-preferred embodiment the abovementioned external transmitter device is a transceiver device, and, for each probe, the means for wirelessly transmitting data-carrying signals comprises the probe's coil, or a second coil, with which each probe is operable to transmit data-carrying signals arising from the sensing electrode(s) to the array of coils by inductive coupling. In turn, the primary coil is operable to transmit data-carrying signals to the external transceiver device by inductive coupling.

In such a manner, data-carrying signals arising from the sensing electrodes can be transmitted efficiently and reliably to the external transceiver device. Moreover, a significantly higher number of recording channels (i.e. sensing electrodes) can be supported, compared to pre-existing systems.

In alternative embodiments, for each probe, the means for wirelessly transmitting data-carrying signals may comprise a wireless transmitter operable to transmit data-carrying signals directly to an external receiver device. For example, the wireless transmitter in each probe may be a Bluetooth low energy transmitter, and the external receiver device may be a compatible Bluetooth receiver in the proximity of the patient's head.

According to a second aspect of the invention there is provided a wireless probe for subdural implantation into or onto the human brain, the probe comprising at least one sensing electrode, a coil for receiving power via inductive coupling, signal processing circuitry coupled to the sensing electrode(s), and means for wirelessly transmitting data-carrying signals. Preferable/optional features of such a probe are as for the probes discussed above, in the context of the overall neural interface arrangement.

According to a third aspect of the invention there is provided an arrangement comprising an array of coils for implantation above the dura, beneath the skull, the array of coils being connected to a primary (e.g. subcutaneous) coil for implantation above the skull. Preferable/optional features of such an arrangement (including the inclusion of a multiplexing chip) are as for the array of coils and the primary coil as discussed above, in the context of the overall neural interface arrangement.

According to a fourth aspect of the invention there is provided a system comprising a neural interface arrangement in accordance with the first aspect of the invention, and a said external transmitter device and an external receiver device; or an external transceiver device.

By way of example, the system may be configured to transmit data from the sensing electrodes to the external receiver/transceiver device at a rate of the order of ~1 Mbps (~1 megabit per second).

The coupling between the external receiver/transceiver device and the primary coil may use an NFC (near field communication) link.

The external receiver/transceiver device may be coupled to a unit configured to process the data arising from the implanted probes and to effect control of a connected device based on said data. Merely by way of two non-limiting examples, it is envisaged that such a connected device could be a motorised wheelchair for a paralysed person, or a voice synthesiser for a person with motor neuron disease who is unable to speak. Other applications are also possible, as those skilled in the art will appreciate (including, for example, taking an output from the sensory cortex).

According to a fifth aspect of the invention there is provided an external device for use with the neural interface arrangement of the first aspect of the invention, or in the system of the fourth aspect of the invention, the device comprising a battery or other power supply means, a coil for inductively coupling with said primary coil, and electronics configured to provide power and control/calibration signals to the implanted probes via said primary coil. Optionally the device may be further configured to receive signals arising from the implanted probes via inductive coupling with said primary coil.

A sixth aspect of the invention provides use of a system in accordance with the fourth aspect of the invention, to control a connected device.

The present principles may also be used to provide electrode stimulation to the brain. Thus, according to a seventh aspect of the invention there is provided an arrangement comprising: a plurality of probes for subdural implantation into or onto a human brain, each probe including a coil for receiving power via inductive coupling, and at least one electrode coupled to the coil; an array of coils for implantation above the dura, beneath the skull, the array of coils being for inductively coupling with the coil of each of the plurality of probes, for transmitting power to the probes; and a primary (e.g. subcutaneous) coil connected to the array of coils, the primary coil being for inductively coupling with an external transmitter device, for receiving power from the external transmitter device; wherein, in use, the primary coil is operable to receive power from the external transmitter device by inductive coupling and to cause the array of coils to transmit power to the plurality of probes by inductive coupling; and wherein, in use, the plurality of probes are operable to cause the electrodes to stimulate the brain.

Optional features of the arrangement according to the seventh aspect of the invention are as set out above in respect of the first aspect of the invention, duly modified so as to relate to stimulating the brain, rather than sensing.

Similarly, according to an eighth aspect of the invention there is provided a probe for subdural implantation into or onto the human brain, the probe comprising a coil for receiving power via inductive coupling, and at least one electrode coupled to the coil, for stimulating the brain in use.

Optional features of the probe according to the eighth aspect of the invention are as set out above in respect of the second aspect of the invention, duly modified so as to relate to stimulating the brain, rather than sensing.

According to a ninth aspect of the invention there is provided a system comprising an arrangement in accordance with the seventh aspect of the invention, and a said external transmitter device.

A tenth aspect of the invention provides use of a system in accordance with the ninth aspect of the invention, to stimulate the brain.

Finally, an eleventh aspect of the invention is a surgical method of installing an arrangement, in accordance with the first or seventh aspects of the invention, into a patient, the method comprising: removing a section of the patient's skull, and associated skin; opening the dura beneath the removed skull; implanting the plurality of probes into or onto the patient's brain; sealing the dura over the implanted probes; and re-fitting the removed skull section (or an artificial replacement therefor), with the array of coils having been installed beneath the skull, above the dura, and the primary coil having been installed beneath the skin, above the skull, or elsewhere on the patients body.

As discussed above, installation of the array of coils beneath the skull and the primary coil above the skull may be facilitated by the array of coils and the primary coil being integrated into a device of unitary form, that may be readily fitted around the removed skull section.

BRIEF DESCRIPTION OF THE DRAWINGS

Embodiments of the invention will now be described, by way of example only, and with reference to the drawings in which.

In the figures, like elements are indicated by like reference numerals throughout.

DETAILED DESCRIPTION OF PREFERRED EMBODIMENTS

The present embodiments represent the best ways known to the Applicant of putting the invention into practice. However, they are not the only ways in which this can be achieved.

Introduction

The present work is based on realizing millimetre-scale neural probes that are completely wireless (both for powering and data transfer), for subdural implantation into the cortex. Several such probes can be manually inserted (i.e. implanted) by a neurosurgeon at the desired locations, in a tetherless, wire-free fashion, and the dura can then be sealed over them, such that no physical components pass through the dura.

By way of further background, the trend for millimetre-sized subdural implants has very much been to attempt wireless communication from the implant device through the dura, skull and skin to an external device, typically using inductive coupling. However due to a significant mismatch between the size of the inductor and the spacing, i.e. the distance between the implant and the external reader, the overall efficiency of the link tends to be very low (of the order of ~1%). The spacing between the implant and the reader in such implementations would typically be of the order of 10-15 mm.

The present work overcomes this bottleneck by taking a 3-tier/2-link approach. A first inductive link communicates across the dura (typically a few hundred microns thick) using matched pairs of millimetre-sized coils, to transfer power to the probes and to receive data from the probes. The millimetre-sized coils above the dura are then multiplexed and connected (via wire) to a second inductive transcutaneous link, which communicates with, and receives power from, an external (e.g. body worn) device that provides a back-end interface.

System Overview

Figure 1:
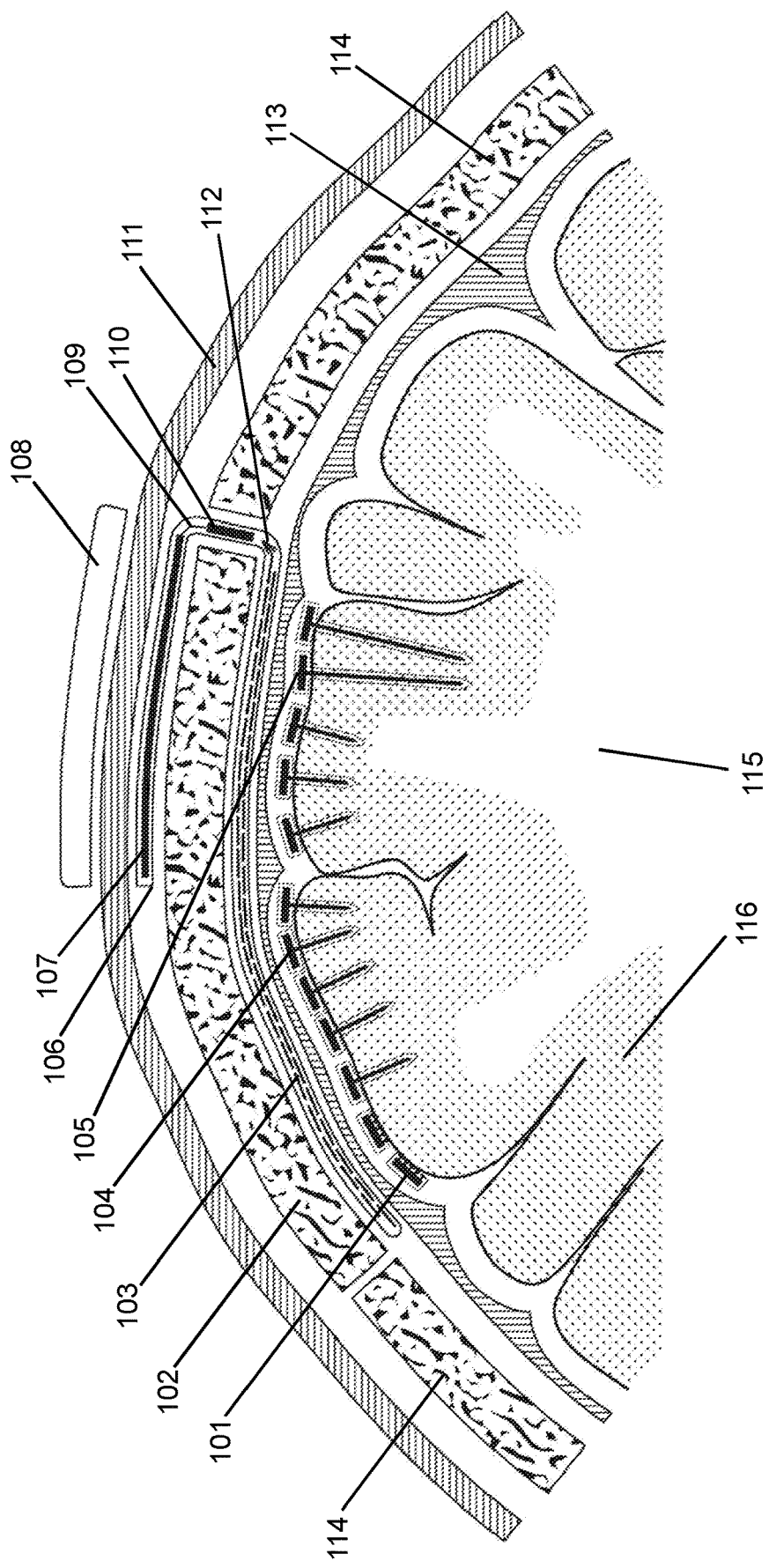
FIG. 1 is a cross-sectional schematic diagram of a system according to the present work.

FIG. 1 is a cross-sectional schematic diagram of a system according to the present work.

Firstly, by way of anatomical context, the human head has an outer surface of skin/tissue/scalp layers 111, beneath which is the skull 114. Beneath the skull 114 is the dura mater (or simply "dura") 113. Under the dura 113 is the brain, which is made up of white matter 115 and grey matter 116.

A section 102 of the skull is removed by a surgeon for installation of the present system, and then returned to position afterwards.

The present system includes a plurality of implantable wireless probes, which, in use, are surgically implanted into the brain, beneath the dura 113. As illustrated in FIG. 1 (and later in FIGS. 2, 3a, 3b and 4), the present work provides a number of different types of implantable probes. Each implantable probe includes at least one electrode (and preferably a plurality of discrete independent electrodes) for sensing the local electrical field potential in respect of each electrode. Preferably each implantable probe also includes a reference electrode, as mentioned above and as discussed in greater detail below.

A first type of implantable probe 101 is for surface monitoring micro-electrocorticography (micro-ECoG), and is positioned on the surface of the grey matter 116.

A second type of implantable probe is a "drawing-pin-like" probe 104, 105 (i.e. broadly in the shape of a drawing pin) for intracortical recording by penetrating into the grey matter 116. A first variant, probe 104, has a relatively short shank length. A second variant, probe 105, has a longer shank length, to reach deeper into the grey matter 116. Alternatively, if implanted near the "folds" of the grey matter 116, a drawing-pin-like probe (especially the longer variant 105) can be inserted parallel to the surface to monitor a certain depth of cells "laterally".

It should be noted that the probes 101, 104, 105, when implanted, do not pass though the dura 113, but are located entirely beneath the dura 113.

Each probe 101, 104, 105 includes a millimetre-scale coil for receiving power, and for transmitting and receiving data-carrying signals, via inductive coupling. Further, each probe 101, 104, 105 also includes active electronics for power management, signal processing and communication, for example in the form of a CMOS (complementary metal-oxide semiconductor) system on a chip.

These, and other, types of implantable probes are discussed in greater detail below, in particular with reference to FIGS. 2, 3a, 3b and 4.

Above the skin/scalp 111, an external transceiver device 108 (separate from the head, and which may be freely movable) is provided to transmit power and control signals to the implanted probes 101, 104, 105, and to receive data from the implanted probes 101, 104, 105. The transmission of the power and control signals and the data between the external transceiver device 108 and the implanted probes 101, 104, 105 is by means of inductive coupling, using first and second inductively-coupled links.

The first and second inductively-coupled links are established by means of an implanted primary coil 107 coupled (in a wired manner) to an array of overlapping millimetre-scale coils 103. The primary coil 107 is relatively large in comparison to an individual millimetre-scale coil.

In the illustrated embodiment the primary coil 107 is a subcutaneous coil, located under the skin 111 above the skull section 102, using relatively short wiring to couple to the array of overlapping millimetre-scale coils 103. However, in alternative embodiments the primary coil 107 may be located elsewhere on the scalp, or anywhere on the head, or indeed anywhere on the body (e.g. on the patient's chest), using wiring of suitable length to couple to the array of overlapping millimetre-scale coils 103. For example, the wiring may pass under the skin and tunnelled to the chest area (e.g. as is done with DBS devices), where the primary coil 107 may then be situated.

The array of overlapping millimetre-scale coils 103 is located above the implanted probes 101, 104, 105, above the dura 113, and beneath the skull 102. The primary coil 107 and the array of overlapping millimetre-scale coils 103 are coupled together via an intermediate multiplexing/telemetry transponder chip 110 and wired connections 109 and 112.

In passing, it should be noted that the probes 101, 104, 105 may be freely positioned into or onto the brain; their precise locations are not critical to the operation of the present system, as long as the probes are covered by the overall array of overlapping millimetre-scale coils 103. Indeed, as is discussed in greater detail below, the fact that the millimetre-scale coils 103 overlap one another in the array provides considerable flexibility in respect of the positioning of the probes, since it mitigates the issue of potential misalignment between the coils in the probes and the coils of the array 103.

The external transceiver device 108 includes a coil that forms an inductively-coupled pair with the primary coil 107, thus forming a first inductively-coupled link. The external transceiver device 108 also contains a battery (or may receive power by means of some other power supply) and electronics for communication/control/processing.

A second inductively-coupled link is formed between the array of millimetre-scale coils 103 and the millimetre-scale coil in each of the probes 101, 104, 105.

Thus, in use, the primary coil 107 provides control/calibration signals and power from the external transceiver device 108 to the implanted probes 101, 104, 105, via the array of overlapping millimetre-scale coils 103, and transmits data from the implanted probes 101, 104, 105 to the external transceiver device 108.

The primary coil 107 is coupled to the array of millimetre-scale coils 103 by means of the multiplexing chip 110 (encapsulated within an insulating material, e.g. silicone rubber), the multiplexing chip 110 being located by the skull 102, above the dura 113. The multiplexing chip 110 is configured to receive power from the primary coil 107, multiplexing to the array of coils 103, and is also for receiving/encoding data (e.g. time division multiplexed) from the implanted probes 101, 104, 105.

Each coil in the array 103 is independently connected to the multiplexing chip 110 via connections 112. The multiplexing chip 110 is connected to the primary coil 107 by means of connection 109.

In a presently-preferred embodiment the array of millimetre-scale coils 103, the multiplexing chip 110, the primary coil 107, and the connections 109 and 112, are all comprised within a transponder device 106 of unitary form (which may for example be coated in flexible silicon encapsulant).

Such a device 106 of unitary form facilitates introduction of the array of coils 103, the multiplexing chip 110 and the primary coil 107 into the patient's head. More particularly, when the skull section 102 is removed to enable the probes 101, 104, 105 to be implanted, the device 106 may be readily fitted around the removed skull section 102, with the array of coils 103 on the underside of the skull section 102, and the primary coil 107 on the outside of the skull section. The removed skull section 102 (or an artificial replacement therefor) may then be re-fitted to the patient's head, with the array of coils 103, the multiplexing chip 110 and the primary coil 107 all in place.

(For completeness, in passing we note that, in other embodiments, the array of millimetre-scale coils 103 may be a separate entity from the primary coil 107, i.e. not provided as a device 106 of unitary form.)

Thus, the sequence of connections which form the overall link between the external transceiver device 108 and the implanted probes 101, 104, 105 is as follows: The external transceiver device 108 is inductively coupled to the primary (e.g. subcutaneous) coil 107 via the first link, and in turn the primary coil 107 is coupled to the array of millimetre-scale coils 103 via the multiplexing chip 110 and connections 109 and 112. Finally, as the second link, the array of millimetre-scale coils 103 is inductively coupled to the implanted probes 101, 104, 105 by means of the coil in each of the probes.

The external transceiver device 108 provides power and control/calibration signals to the implanted probes 101, 104, 105 via inductive coupling, via the primary coil 107, the multiplexing chip 110, and the array of millimetre-scale coils 103; the implanted probes 101, 104, 105 have no other source of power.

In the opposite direction, signals generated by the implanted probes 101, 104, 105 are transmitted via inductive coupling to the external transceiver device 108 via the array of millimetre-scale coils 103, the multiplexing chip 110, and the primary coil 107.

The external transceiver device 108 may be coupled (via a wired or wireless connection) to a system that processes the data arising from the implanted probes 101, 104, 105 and in turn effects motor control of an assistive device based on said data.

Implantable Probes

Exemplary designs of the implantable wireless probes will now be described in more detail.

Figure 2:
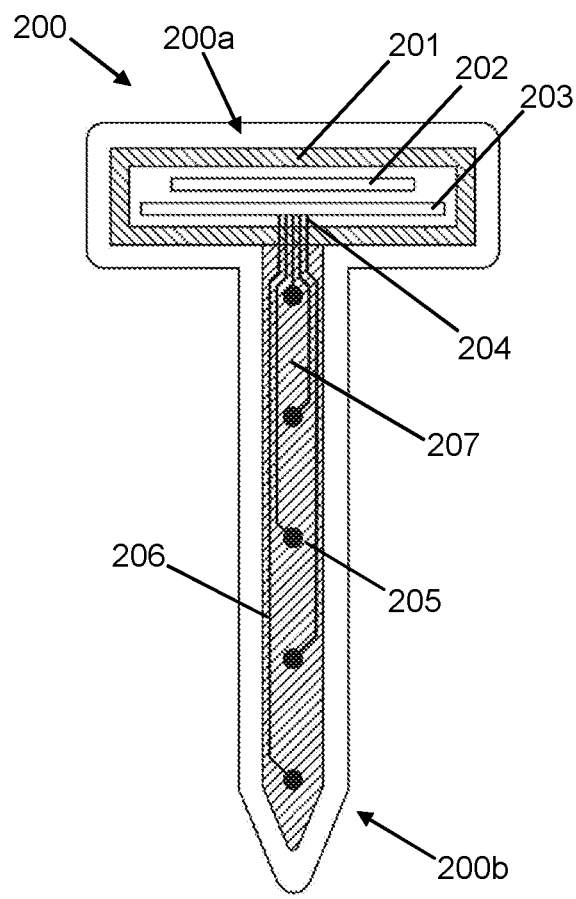
FIG. 2 illustrates, in longitudinal cross-section, a first drawing-pin-like implantable probe, with a rigid shank, for intracortical recording.
Figure 4:
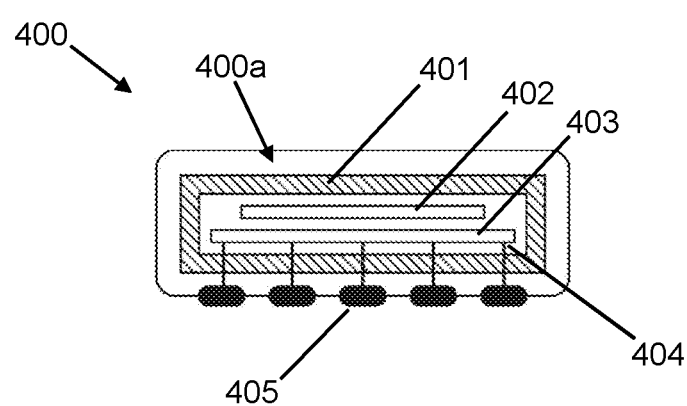
FIG. 4 illustrates, in cross-section, a probe with planar electrodes, for surface recording.
Figure 3A:
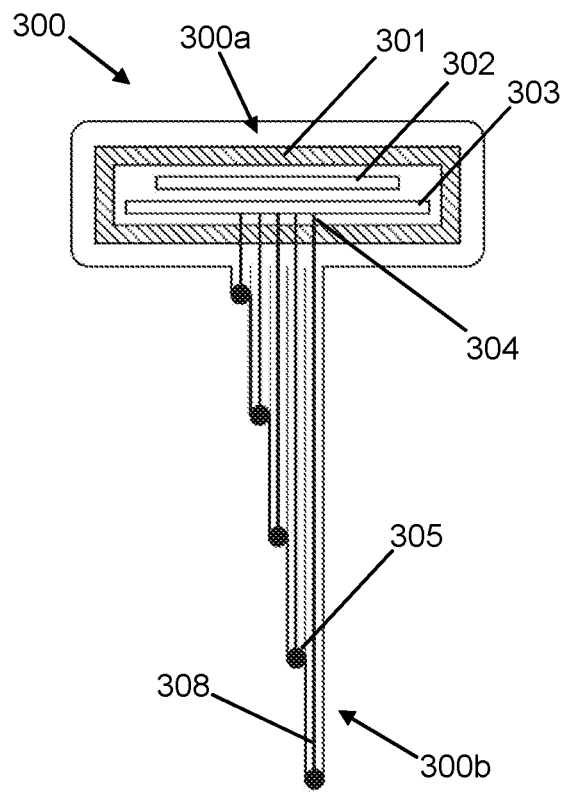
FIG. 3a illustrates, in longitudinal cross-section, a second drawing-pin-like implantable probe, with a non-rigid shank, for intracortical recording.
Figure 3B:
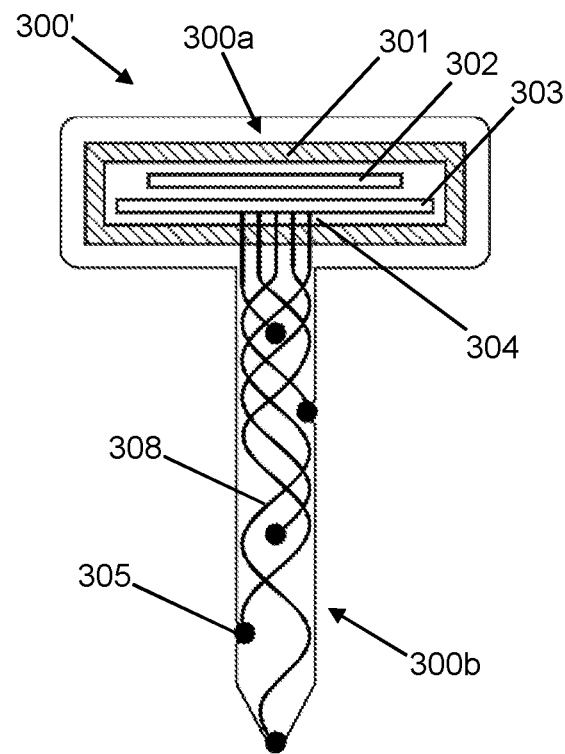
FIG. 3b illustrates, in longitudinal cross-section, an alternative configuration of the drawing-pin-like implantable probe of FIG. 3a, with either a rigid or non-rigid shank, for intracortical recording, but in this case with the shank comprising a braided arrangement of wires.

FIGS. 2, 3a and 4 illustrate, in cross-section, three different variants of our implantable probes, and FIG. 3b illustrates an alternative configuration of the variant of FIG. 3a.

FIG. 2 illustrates a first drawing-pin-like probe 200 for intracortical recording, having a rigid shank and insulated conductors connecting to the electrode sites (corresponding to probes 104, 105 in FIG. 1).

FIG. 3a illustrates a second drawing-pin-like probe 300 for intracortical recording, having a shank made up of flexible and/or soft insulated wires connecting to the electrode tips, instead of a rigid shank (not expressly illustrated in FIG. 1, but may be used instead of probe 104 or probe 105).

FIG. 3b illustrates an alternative configuration 300' of the drawing-pin-like implantable probe of FIG. 3a, again having a shank made up of flexible and/or soft insulated wires connecting to the electrode tips, but in this case the constituent wires of the shank are in a braided arrangement (rather than in the substantially parallel or linear arrangement depicted in FIG. 3a). In this alternative configuration 300' the position of the electrode tips may be determined by some pre-formed structure, whereas probe 300 of FIG. 3a is simply formed from a bundle of wires. The shank of alternative probe 300' may be either rigid or non-rigid.

FIG. 4 illustrates a probe 400 (corresponding to probe 101 in FIG. 1) without a shank, with planar electrodes, for surface recording, e.g. micro-electrocorticography (micro-ECoG).

Taking these exemplary probe designs in turn, and with reference initially to FIG. 2, the first drawing-pin-like probe 200 is typically millimeter-scale (for example, 5 mm long and 3 mm head diameter), and consists of two main parts: a head 200a and a shank 200b.

The head 200a incorporates active electronics 203 for instrumentation, power management and communication, and a millimetre-scale coil 202 for inductive coupling with the above-described coil array 103. The electronics are preferably formed as a CMOS system on a chip, with a silicon-based "lid" or "cap" that is bonded to the CMOS chip using low temperature (i.e. CMOS compatible) wafer bonding methods (for example, eutectic bonding) to create a hermetically-sealed micropackage 201 (Saeidi, 2013). This protects the electronics from moisture and ensures chronic reliability. The head 200a may be any shape (e.g. circular, octagonal, square).

The shank 200b is essentially a pin (either round cylindrical, rectangular flat surfaced, or other) with multiple independent electrodes 205 positioned at specific locations, e.g. at a range of depth positions along the shank 200b, for sensing the local electrical field potential in respect of each electrode in use. In certain embodiments the electrodes 205 are bare metal such as to provide a galvanic connection to the surrounding tissue in use, via the formation of an electrode/electrolyte interface (although in alternative embodiments the metals may be coated rather than left in their bare form). The electrode material is selected to be inert, e.g. gold, platinum, tungsten or niobium. Each electrode 205 is wired (inside the "pin") to the instrumentation/read-out electronics 203 in the head 200a, via interconnections 206 and hermetically-sealed feedthroughs 204. The wiring of the interconnections 206 may be patterned using photolithography, or alternatively may be wired inside the shank to the feedthroughs 204. The feedthroughs 204 may advantageously use through-silicon-via (TSV) technology, and/or an interposer layer (e.g. either glass or silicon).

In the first drawing-pin-like probe 200 the rigid shank 200b includes a fabricated core 207 on which the electrodes 205 are mounted, and in which the interconnections 206 are located. The core 207 may for example be machined out of substrate material.

By virtue of the rigid shank 200b, the surgeon can implant the probe 200 simply by pushing it into the brain tissue.

With reference now to FIG. 3a, the second drawing-pin-like probe 300 has a head 300a that is substantially identical to head 200a in FIG. 2, but a different arrangement in respect of the shank 300b.

Thus, the head 300a incorporates active electronics 303 for instrumentation, power management and communication, and a millimetre-scale coil 302 for inductive coupling with the above-described coil array 103. As described above in relation to FIG. 2, the electronics are preferably formed as a CMOS system on a chip, with a silicon-based "lid" or "cap" that is bonded to the CMOS chip using low temperature (i.e. CMOS compatible) wafer bonding methods (for example, eutectic bonding) to create a hermetically-sealed micropackage 301. The head 300a may be any shape (e.g. circular, octagonal, square).

With regard to the shank 300b, this is essentially formed as a bundle of flexible and/or soft insulated conducting (metal) wires 308, with their tips exposed to form the electrodes 305. Examples of suitable metals for the wires 308 and electrodes 305 are as given above in respect of the electrodes 205 of the first probe 200. The wires 308 are of different lengths, such that the electrodes 305 are at a range of depth positions, for sensing the local field potential in respect of each electrode in use. The wires 308 are insulated using a biocompatible insulator such as Teflon or silicone. The wires 308 are connected to the electronics 303 in the head 300a via feedthroughs 304, through hermetic sealing, e.g. utilizing through-silicon-via (TSV) technology, and/or an interposer layer (e.g. either glass or silicon).

For implantation of the probe 300, it will be appreciated that the shank 300b, being made of a bundle of flexible and/or soft wires 308, cannot be used to pierce/guide itself through the brain tissue. Thus, for implantation, a guide hole may first need to be made by the surgeon (similar to DBS) and then the probe 300 inserted. Alternatively, in another embodiment, a hole may be provided through the whole probe (i.e. its head would be like a doughnut), through which a pin may be inserted for implantation, and then removed once the probe has been implanted.

In the probe 300 illustrated in FIG. 3a, the bundle of wires 308 that form the non-rigid shank 300b are linear and substantially parallel to one another. However, in alternative configurations of the probe 300, the wires 308 may be arranged differently. An example of such an alternative configuration is illustrated in FIG. 3b, in which the shank 300b of the alternative probe 300' comprises wires 308 in a braided arrangement. By braiding the wires 308 in such a manner, greater strength and integrity of the shank 300b may be achieved. With the braided probe 300' the position of the electrode tips 305 may be determined by some pre-formed structure, whereas probe 300 of FIG. 3a is simply formed from a bundle of wires. Such a pre-formed structure for the probe 300' may incorporate predetermined locations (e.g. using recesses) for the electrode tips 305, thus defining the positions of the recording sites. The shank 300b of the braided probe 300' may be either rigid or non-rigid. It is to be understood that all subsequent references herein to probe 300 of FIG. 3a equally apply to probe 300' of FIG. 3b.

It should also be noted that, with the drawing-pin-like probes as illustrated for example in FIGS. 2 and 3a, the electrodes (e.g. 205 and 305) may be uniformly distributed along the length of the shank (e.g. as illustrated). However, in alternative variants, the electrodes may be non-uniformly distributed (e.g., if desired, all near the distal tip of the probe).

Turning now to FIG. 4, this shows a probe 400 with planar electrodes 405, essentially consisting of a head 400a only, without a shank, for surface recording. The head 400a is substantially identical to head 200a in FIG. 2 and head 300a in FIG. 3a.

Thus, the head 400a incorporates active electronics 403 for instrumentation, power management and communication, and a millimetre-scale coil 402 for inductive coupling with the above-described coil array 103. As described above in relation to FIGS. 2 and 3a, the electronics are preferably formed as a CMOS system on a chip, with a silicon-based "lid" or "cap" that is bonded to the CMOS chip using low temperature (i.e. CMOS compatible) wafer bonding methods (for example, eutectic bonding) to create a hermetically-sealed micropackage 401. The head 400a may be any shape (e.g. circular, octagonal, square).

The planar electrodes 405 are disposed on the underside of the head and connected to the electronics 403 in the head 400a via feedthroughs 404, through hermetic sealing, e.g. utilizing through-silicon-via (TSV) technology, and/or an interposer layer (e.g. either glass or silicon). It will be appreciated that the electrodes 405, being for surface recording, are all at the same depth, but are at different lateral positions across the breadth of the probe, to sense the local field potential in respect of each electrode in use.

With regard to all three probes 200, 300 and 400 of FIGS. 2, 3a and 4, after construction the entire probe may be passivated in a protective insulator (e.g. silicon dioxide or silicon nitride) and then coated in a biocompatible (e.g.

silicone) encapsulant, such that only the electrode recording sites 205, 305, 405 are exposed.

Chip-Scale Micropackaging

Figure 5A:
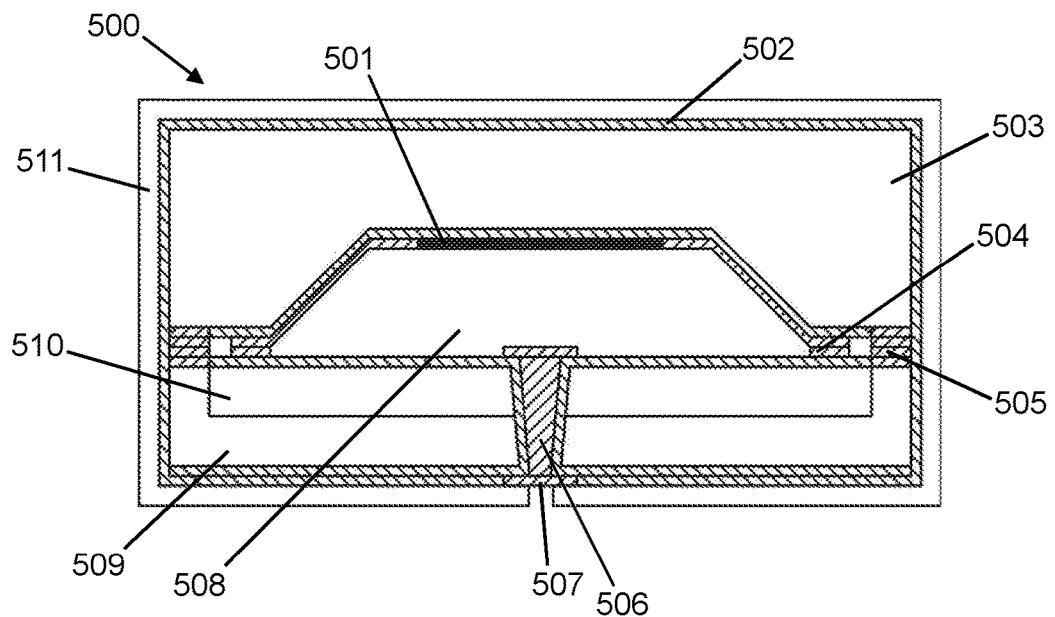
FIG. 5a illustrates, in cross-section, an exemplary arrangement of chip-scale micropackaging.

FIG. 5a illustrates, in cross-section, an exemplary arrangement of chip-scale micropackaging 500, providing hermetic sealing with feedthroughs, as may be employed in the heads (e.g. 200a, 300a, 400a) of the above-described probes (e.g. 200, 300, 400).

The micropackaging 500 includes a millimetre-scale coil 501 (corresponding to coil 202 in FIG. 2, coil 302 in FIG. 3a, and coil 402 in FIG. 4) and a CMOS chip comprising active CMOS electronics 510 (corresponding to electronics 203 in FIG. 2, electronics 303 in FIG. 3a, and electronics 403 in FIG. 4) disposed on a CMOS substrate 509. A dry gas cavity 508 is provided between the coil 501 and the CMOS substrate 509.

A silicon "lid" or "cap" 503 is bonded to the CMOS chip to provide a hermetic micro-package. This can be either a passive silicon chip, with an etched cavity, or an active CMOS die. An electrical connection 504 is provided between the CMOS chip and the silicon lid 503, and a hermetic seal 505 is formed via wafer-scale bonding.

The above assembly is surrounded by a passivation/insulating layer 502 (e.g. silicon dioxide, silicon nitride, etc), which is encapsulated by a biocompatible encapsulant 511, e.g. silicone rubber.

A through-silicon-via (TSV) 506 is employed to provide a hermetically-sealed connection between the outside of the micropackaging (e.g. the above-described electrodes) and the electronics inside the micropackaging. This uses an external bondpad 507, outside the hermetic seal.

Figure 5B:
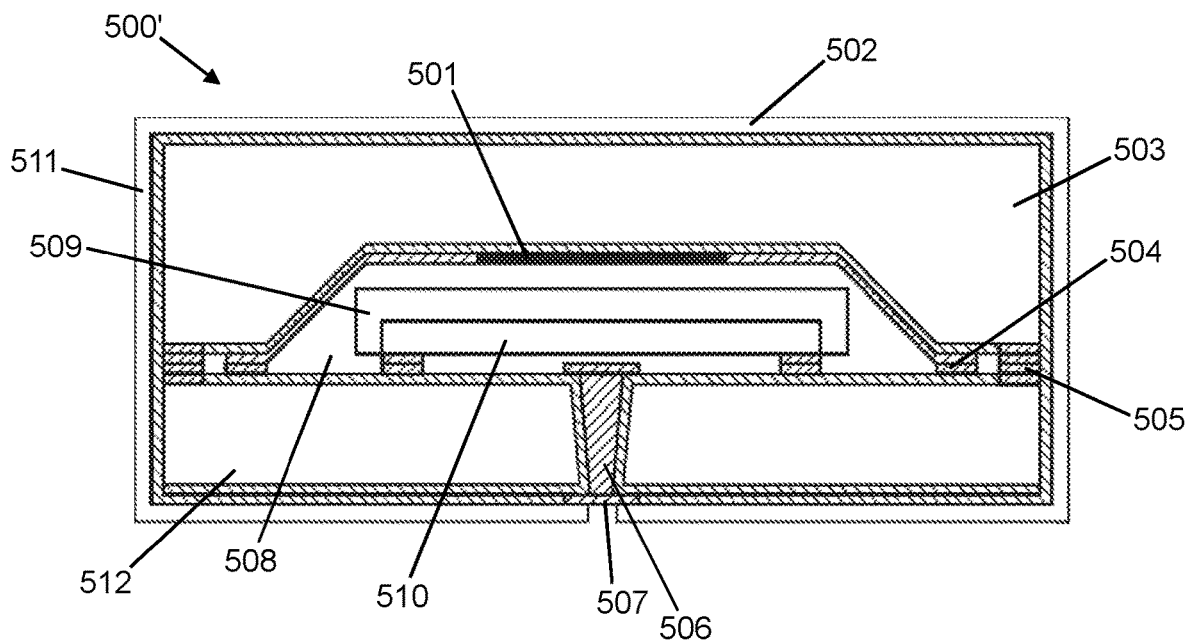
FIG. 5b illustrates, in cross-section, an alternative configuration of the chip-scale micropackaging of FIG. 5a, in this case using an interposer layer to achieve feedthroughs.

In alternative embodiments of the micropackaging, an interposer layer (e.g. either glass or silicon) may be used to achieve feedthroughs, instead of, or in addition to, a through-silicon-via (TSV). FIG. 5b illustrates an example of such alternative micropackaging 500', including an interposer layer 512, with the CMOS integrated circuit 510 (disposed on a CMOS substrate 509) connected internally.

Neural Interface Electronics

The above-described CMOS electronics 510, within the head of each probe 200, 300, 400, functions as a system-on-chip and includes three main "modules":

(1) front end instrumentation—that for each electrode will amplify the signal, condition (i.e. filter) the signal, and digitize it;
(2) power management—that for each probe receives and rectifies power through the inductive link, and regulates the power to provide the electronics with a stable DC supply;
(3) communication—providing asymmetrical full-duplex communication in respect of each probe (i.e. receiving commands and/or calibration signals from the external transceiver device 108; and sending recorded data, or probe "status" or "health" information, back to the external transceiver device 108).

Figure 6:
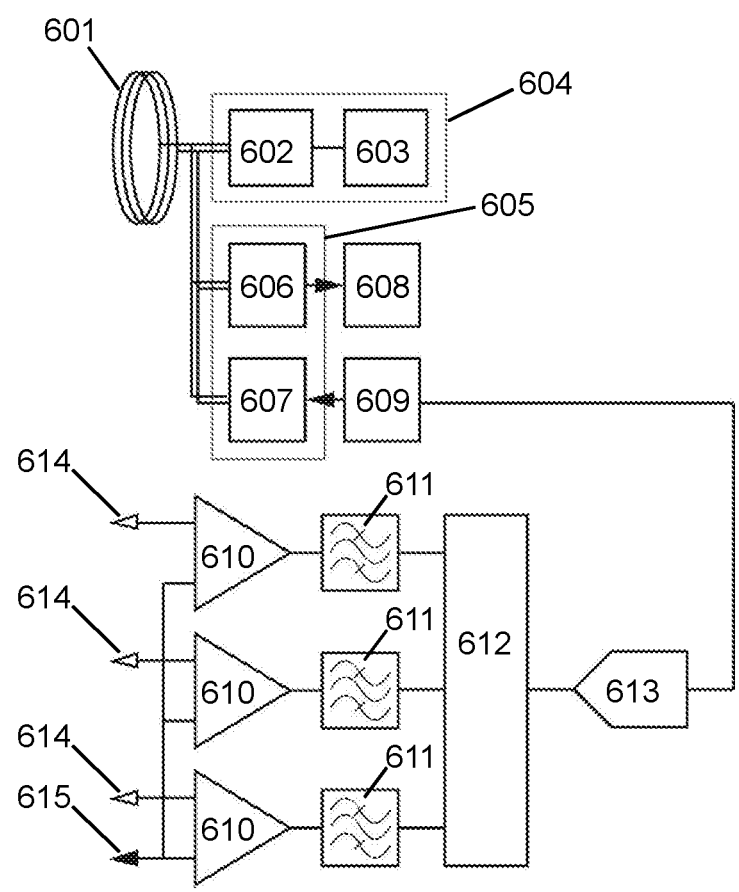
FIG. 6 illustrates exemplary electronics as may be employed within the implantable probes.

FIG. 6 illustrates exemplary electronics as may be employed within the head of each probe 200, 300, 400.

A millimetre-scale coil 601 (corresponding to coil 202 in FIG. 2, coil 302 in FIG. 3a, coil 402 in FIG. 4, and coil 501 in FIGS. 5a and 5b) is connected to a power management module 604 and a communication module 605. As discussed above, the coil 601 is configured to inductively couple with the coil array 103 (FIG. 1) to form the second inductive link. In use, by means of inductive coupling, the coil 601 receives power and control/calibration signals from the external transceiver device 108, via the primary (e.g. subcutaneous) coil 107 and then the coil array 103. Also by means of inductive coupling, signals arising from the probe's electrodes are transmitted by the coil 601, via the coil array 103 and then the primary coil 107, to the external transceiver device 108.

The power management module 604 includes rectification circuitry 602 and regulation circuitry 603.

The communication module 605 includes downlink circuitry 606 and uplink circuitry 607.

The downlink circuitry 606 is connected to configuration and control circuitry 608, to configure and control the operation of the probe. The functionality of the "control" aspect of the circuitry 608 includes sending the probe "commands" to execute certain functions—such as, for example, "record 1000 samples from channel 1", or "continuously stream raw data from all channels". The functionality of the "configuration" aspect of the circuitry 608 includes making settings (or setting different modes of operation) for each of the sub-blocks—such as, for example, setting amplifier gain settings for each channel independently, setting filter frequency settings, setting the analogue-to-digital sampling rate, totally disabling certain channels, enabling/disabling compression, etc.

The uplink circuitry 607 is connected to processing and encoding circuitry 609, which processes and encodes signals arising from the probe's various electrodes.

The probe electronics further include sensing electrode inputs 614 connected to the probe's various sensing electrodes (e.g. electrodes 205, 305 and 405 as described above) and a reference electrode input 615 connected to a reference electrode (which may for example be located at the distal tip of the probe, i.e. the end furthest from the head, or elsewhere on the probe). Typically the reference electrode has a lower impedance than the sensing electrodes.

Each sensing electrode input 614 is connected to a respective low noise amplifier 610. The reference electrode input 615 is also connected to each low noise amplifier 610, such that the signal from the reference electrode input 615 is subtracted from the signal from each sensing electrode input 614.

The output of each low noise amplifier 610 is passed through a bandpass filter 611, the output of which is provided to a multiplexer and buffer 612. The output of the multiplexer and buffer 612 is then fed to an analogue-to-digital (A/D) converter 613.

The output of the A/D converter 613 is then fed to the abovementioned processing and encoding circuitry 609, and thence to the uplink circuitry 607 for transmission by the coil 601, by means of inductive coupling (via the coil array 103, the multiplexing chip 110, and the primary coil 107) to the external transceiver device 108.

Multiplexing Module (Intermediate Tier)

An exemplary multiplexing chip (or "module") 110 will now be described in more detail. This intermediate "module" 110 has the purpose of interfacing the many freely-positioned implanted probes as described above (e.g. 101, 104, 105, 200, 300, 400) with the single external transceiver device 108, and provides significantly improved link efficiency (>25+%) compared to a 2-tier/single link (~1%).

As those skilled in the art will appreciate, key challenges of any inductive link are:

(1) spacing between link pair—addressed through the 3-tier arrangement described above;
(2) load regulation—this can be addressed using several techniques described in literature (Jow and Ghovanloo, 2010); and
(3) misalignment. The problem of misalignment here is addressed by using the overlapping array of coils 103

(embedded within a silicone sheet) that is laid down over the dura 113. In this way, through mass-redundancy, for any position of each implanted probe, there will be at least one coil within the coil array 103 that is aligned adjacent to the head of the respective probe, so as to be able to establish inductive coupling between said coil within the coil array 103 and the coil within the head of the probe.

The coil array 103 is connected to the multiplexing chip 110 that, on initial setup, interrogates all the coils in the array 103 to establish which are best aligned and where the implanted probes are positioned. For subsequent operation the multiplexing chip 110 simply sequences through this subset of coils, in essence performing time division multiplexing (TDM). The multiplexing chip 110 subsequently encodes the multiplexed recordings into a single bitstream and can additionally perform compression to improve the bandwidth utilisation. This bitstream is then transmitted via the uplink telemetry using the larger transcutaneous coil pair (i.e. the primary coil 107, and the coil in the external transceiver device 108). The transcutaneous inductive telemetry may advantageously utilize a carrier frequency in the region of 1-20 MHz, compatible with NFC protocols (e.g. 13.56 MHz).

The external transceiver device 108 provides power to the multiplexing chip 110 via inductive coupling, via the primary coil 107; the multiplexing chip 110 has no other source of power.

Summary of System Architecture

Figure 7:
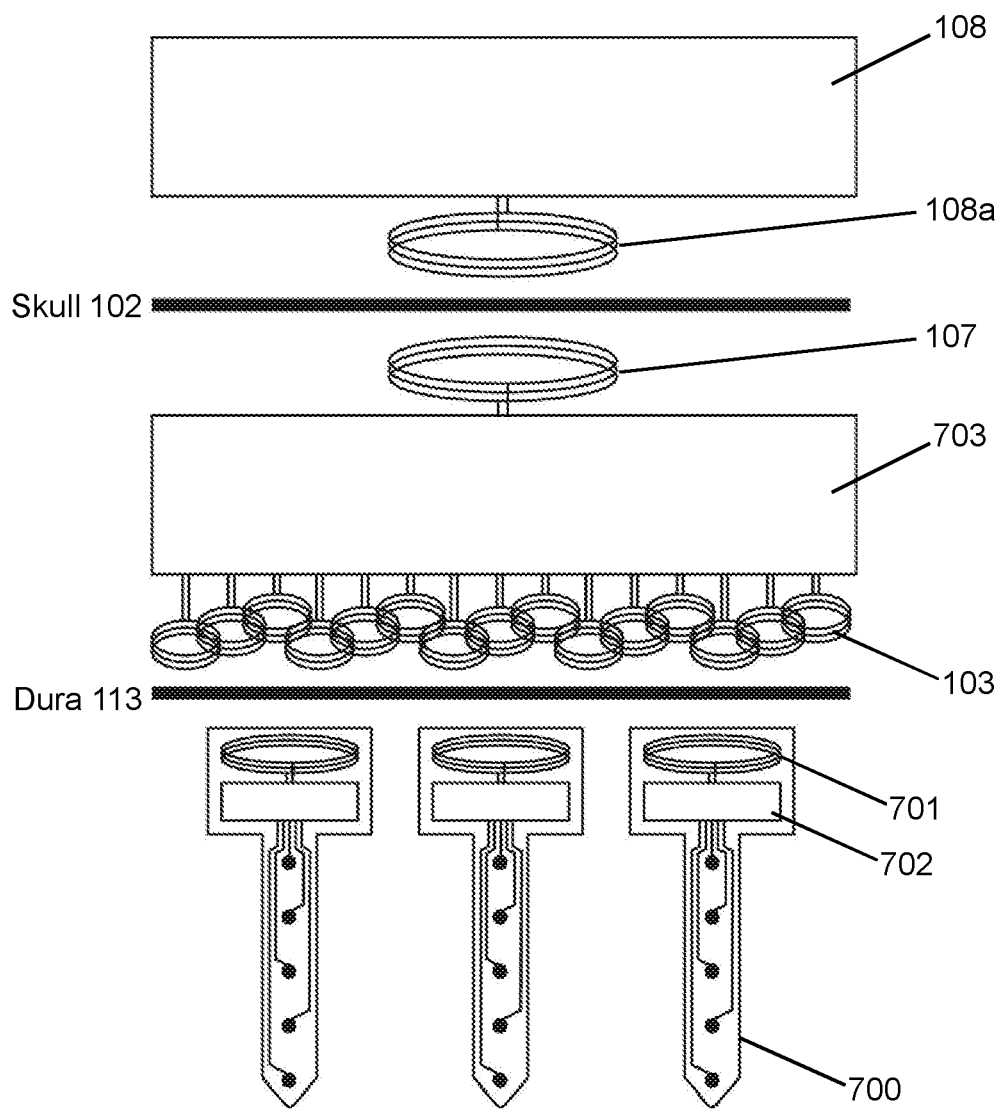
FIG. 7 is a schematic cross-sectional diagram summarising the system architecture according to the present work.

FIG. 7 is a schematic cross-sectional diagram summarising the architecture of the above-described system.

Outside the skull 102 is the external transceiver device 108, having a coil 108a that inductively couples with the primary (e.g. subcutaneous) coil 107.

Above the dura 113, the primary coil 107 is connected to the array of overlapping millimetre-scale coils 103, by means of electrical circuitry 703 which includes the above-described multiplexing chip 110. (NB—as shown in FIG. 1, the primary coil 107 is, in practice, typically located above the skull 102, under the skin 111, as a subcutaneous coil, but merely for the sake of clarity of the diagram in FIG. 7 the primary coil 107 is shown here as being beneath the skull.)

Beneath the dura 113, a plurality of probes 700 (e.g. the above-described probes 101, 104, 105, 200, 300, 400) are implanted into or onto the brain ("onto" being in respect of the above-described surface-mounted probes 101, 400). Each probe 700 includes a millimetre scale coil 701 (e.g. corresponding to coil 202 in FIG. 2, coil 302 in FIG. 3a, coil 402 in FIG. 4, coil 501 in FIGS. 5a and 5b, or coil 601 in FIG. 6) and a CMOS chip comprising active CMOS electronics 510 (e.g. corresponding to electronics 203 in FIG. 2, electronics 303 in FIG. 3a, electronics 403 in FIG. 4, or the circuitry shown in FIG. 6). The millimetre scale coil 701 of each probe 700 inductively couples, across the dura 113, with a suitably-positioned coil of the overlapping millimetre-scale coil array 103.

Indicative Bandwidth Example

To illustrate an exemplary data transfer rate in respect of the present work, assume the following:

All channels are observing local field potential (LFP) recordings with a signal bandwidth of 100 Hz (therefore to satisfy Nyquist, a sampling rate of 250 Hz=250 samples/s)

Probe shanks are 5 mm long with electrodes positioned at 0.5 mm intervals (thus 10 sensing electrodes and one reference electrode per probe)

Data is digitized, i.e. sampled at 10-bit resolution

This gives 250 Hz×10-bit per sample×10 sensing electrodes per probe=25 kbps data rate per probe.

A configuration using 100 implanted probes, each having 10 sensing electrodes (i.e. 1000 channel recording overall), would thus require a 2.5 Mbps data rate (i.e. 100×25 kbps).

Assuming a further 20% overhead for encoding, error detection/correction, etc. would result in a data rate of 3 Mbps (for essentially raw data—with no compression).

Thus using an NFC link utilizing a 13.56 MHz carrier would require below a 25% data-to-carrier ratio; that can be easily achieved using standard encoding techniques (e.g. BPSK, FSK, ASK, etc.).

Possible Modifications and Alternative Embodiments

Detailed embodiments have been described above, together with some possible modifications and alternatives. As those skilled in the art will appreciate, a number of additional modifications and alternatives can be made to the above embodiments whilst still benefiting from the inventions embodied therein.

For example, the electrodes on the implantable probes can be configured to splay outwards, into an extended position, once the probe has been implanted in/on the brain, thereby improving the retention of the electrodes in the brain tissue. This may be achieved by spring-biasing the electrodes into the extended position but initially holding them in a retracted position, for example by providing a biodegradable or dissolvable coating (e.g. made of sugar) around the probe. In use, once the probe has been implanted, the coating dissolves or degrades, enabling the electrodes to spring outwards, from the retracted position to the extended position.

In the above examples a single coil in the head of each probe is used for inductive coupling with the array of coils above the dura. However, in alternative embodiments each probe may have two small coils, one for the reception of power by inductive coupling with said array of coils, and a separate coil for the transmission of data by inductive coupling with said array of coils.

In the above examples, data-carrying signals arising from the sensing electrodes are transmitted to the external transceiver device by inductive coupling, via said array of coils and the primary (e.g. subcutaneous) coil. Thus, with respect to each probe, the probe's coil, or a second coil, functions as means for wirelessly transmitting the data-carrying signals.

However, in alternative embodiments, other means for wirelessly transmitting data-carrying signals can be provided. In particular, the means for wirelessly transmitting data-carrying signals may comprise a wireless transmitter operable to transmit data-carrying signals directly to an external receiver device. For example, the wireless transmitter in each probe may be a Bluetooth low energy transmitter, and the external receiver device may be a compatible Bluetooth receiver in the proximity of the patient's head.

In the above examples, through-silicon-via (TSV) technology is principally used for the feedthroughs in the probes, to provide a hermetically-sealed connection between the electrodes outside of the micropackaging and the electronics inside the micropackaging. However, an alternative approach to using TSV technology for the feedthroughs is to utilise the conductors within the inter-metal dielectrics (IMDs) available in CMOS technology. This would avoid having to post-process the CMOS wafers to achieve the TSVs. Using this alternative approach, the external connections would be routed using the deeper metal (or polysilicon) layers under the hermetic seal to bondpads (or connection points) at the periphery of the chip (outside the hermetic seal). The top (and higher) metal layers would still be required to form the ring to form the hermetic seal. Thus, in effect, with this alternative approach the interconnections are "tunnelled" under the hermetic seal, through the IMDs. An advantage of this alterative approach is it does not need extra processing (in contrast to TSV technology). However, an advantage of TSV technology is that a 2D array of connection points can be achieved, as compared to just perimeter connections. Yet another approach for the feedthroughs is to use an interposer layer, as discussed above.

Alternative Functionality, for Providing Stimulation to the Brain

The above examples primarily relate to relaying electrical signals from the brain to an external device or system, for example for the purpose of effecting motor control of an external device, or for effecting control of a speech synthesiser, or for taking an output from the sensory cortex.

However, the present principles may alternatively (or in addition) be used to provide stimulation to the brain, instead of sensing brain activity. Thus, the present work also provides an arrangement comprising: a plurality of probes for subdural implantation into or onto a human brain, each probe including a coil for receiving power via inductive coupling, and at least one electrode coupled to the coil; an array of coils for implantation above the dura, beneath the skull, the array of coils being for inductively coupling with the coil of each of the plurality of probes, for transmitting power to the probes; and a primary (e.g. subcutaneous) coil connected to the array of coils, the primary coil being for inductively coupling with an external transmitter device, for receiving power from the external transmitter device; wherein, in use, the primary coil is operable to receive power from the external transmitter device by inductive coupling and to cause the array of coils to transmit power to the plurality of probes by inductive coupling; and wherein, in use, the plurality of probes are operable to cause the electrodes to stimulate the brain.

Optional features of this alternative arrangement are as set out above in respect of the above-described "sensing" embodiments, but duly modified so as to relate to stimulating the brain, rather than sensing.

Figure 8:
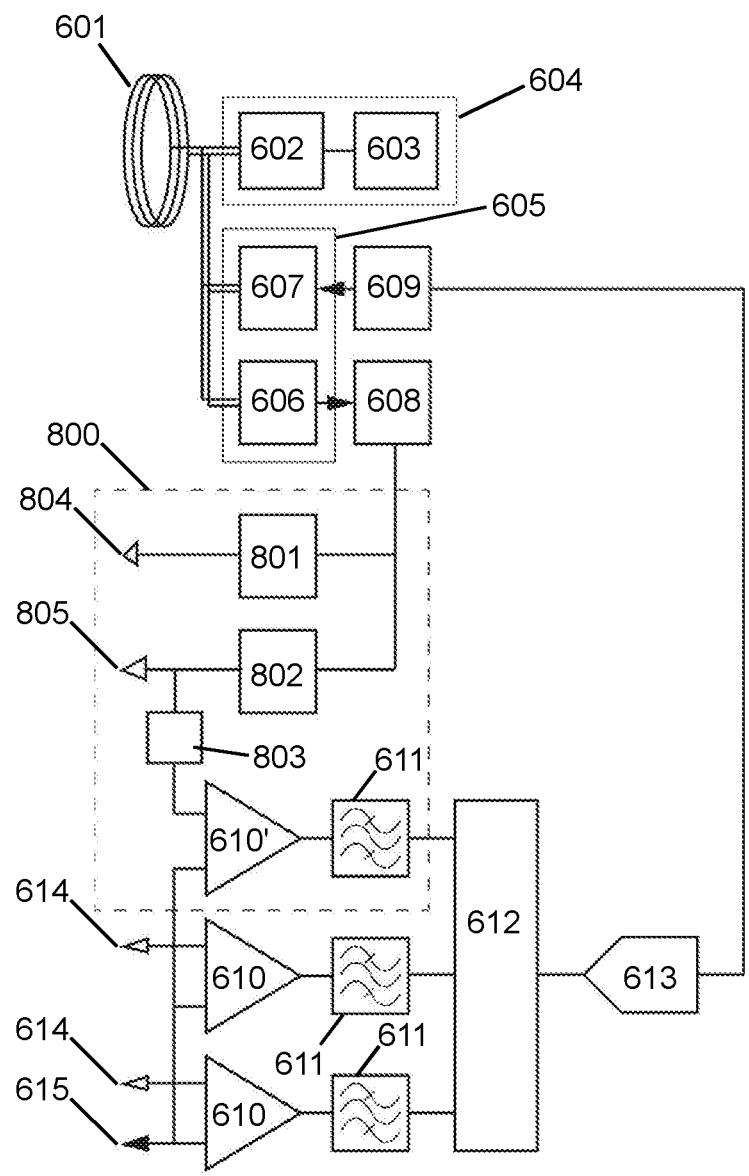
FIG. 8 illustrates a variant of the electronics of FIG. 6, as may be employed within the implantable probes—in this case including additional circuitry to provide the probe with dual sensing and stimulation capabilities.

FIG. 8 illustrates a variant of the electronics of FIG. 6, as may be employed within the implantable probes. In FIG. 8, certain elements as present in FIG. 6 (including sensing electrode inputs 614 and reference electrode input 615) are indicated by like reference numerals, and their functionality is substantially as described above in relation to FIG. 6. However, the electronics of FIG. 8 also include additional circuitry 800 to provide the probe with dual sensing and stimulation capabilities.

In this example, the electronics of FIG. 8 provide two sensing channels (exclusively sensing), one channel that can be for either stimulation or sensing, and one that is exclusively for stimulation.

In more detail, the additional circuitry 800 includes stimulation circuits 801 and 802, both of which are connected to (and under the control of) the configuration and control circuitry 608. Stimulation circuit 801 is connected to a stimulation electrode 804 (more than one such electrode may be provided), whereas stimulation electrode 802 is connected to a multifunctional sensing and/or stimulation electrode 805 (again, more than one such electrode may be provided).

An isolation switch/isolation circuitry 803 (under the control of the configuration and control circuitry 608) is provided between the multifunctional electrode 805 and a respective low noise amplifier 610'. When the isolation switch/circuitry 803 is "open", the multifunctional electrode 805 functions as a stimulation electrode, in the same manner as stimulation electrode 804. On the other hand, when the isolation switch/circuitry 803 is "closed", the multifunctional electrode 805 functions as a sensing electrode, in the same manner as the sensing electrodes that are connected to inputs 614 (i.e. with electrode 805 feeding in to low noise amplifier 610', along with the reference electrode input 615).

It will of course be appreciated that, instead of the probes having dual sensing and stimulation functionality, in yet another variant the probes may have only stimulation functionality, for providing electrical stimulation to the brain using energy conveyed to the probe by inductive coupling from an external transmitter device via the above-described primary (e.g. subcutaneous) coil and the array of coils.

REFERENCES

[Bansal, 2012] Bansal, A. K., Truccolo, W., Vargas-Irwin, C. E., & Donoghue, J. P. (2012). Decoding 3D reach and grasp from hybrid signals in motor and premotor cortices: spikes, multiunit activity, and local field potentials. *Journal of neurophysiology,* 107(5), 1337-1355.

[Baranauskas, 2014] Baranauskas, G. (2014). What limits the performance of current invasive brain machine interfaces?. *Frontiers in systems neuroscience,* 8.

[Buzsaki, 2012] BuzsAki, G., Anastassiou, C. A., & Koch, C. (2012). The origin of extracellular fields and currents-EEG, ECoG, LFP and spikes. Nature reviews neuroscience, 13(6), 407-420.

[Campbell, 1991] Campbell, P. K., Jones, K. E., Huber, R. J., Horch, K. W., & Normann, R. A. (1991). A silicon-based, three-dimensional neural interface: manufacturing processes for an intracortical electrode array. *Biomedical Engineering, IEEE Transactions on,* 38(8), 758-768.

[Chae, 2009] Chae, M. S., Yang, Z., Yuce, M. R., Hoang, L., & Liu, W. (2009). A 128-channel 6 mW wireless neural recording IC with spike feature extraction and UWB transmitter. *Neural Systems and Rehabilitation Engineering, IEEE Transactions on,* 17(4), 312-321.

[Flint, 2013] Flint, R. D., Wright, Z. A., Scheid, M. R., & Slutzky, M. W. (2013). Long term, stable brain machine interface performance using local field potentials and multiunit spikes. *Journal of neural engineering,* 10(5), 056005.

[Gibson, 2013] Gibson, S., Judy, J. W., & Marković, D. (2013). An FPGA-based platform for accelerated offline spike sorting. *Journal of neuroscience methods,* 215(1), 1-11.

[Hall, 2014] Hall, T. M., Nazarpour, K., & Jackson, A. (2014). Real-time estimation and biofeedback of single-neuron firing rates using local field potentials. *Nature communications,* 5.

[Hara, 2013] Hara, S. A., Kim, B. J., Kuo, J. T., Lee, C. D., Gutierrez, C. A., Hoang, T., . . . & Meng, E. (2013, November). Perforated 2×2 Parylene sheath electrode array for chronic intracortical recording. In *Neural Engineering (NER), 2013 6th International IEEE/EMBS Conference on* (pp. 645-648). IEEE.

[Harris, 2000] Harris, K. D., Henze, D. A., Csicsvari, J., Hirase, H., & Buzsáki, G. (2000). Accuracy of tetrode spike separation as determined by simultaneous intracellular and extracellular measurements. *Journal of neurophysiology*, 84(1), 401-414.

[Harrison, 2003] Harrison, R. R., & Charles, C. (2003). A low-power low-noise CMOS amplifier for neural recording applications. *Solid-State Circuits, IEEE Journal of*, 38(6), 958-965.

[Hochberg, 2012] Hochberg L R, Bacher D, Jarosiewicz B, Masse N Y, Simeral J D, Vogel J, Haddadin S, Liu J, Cash S S, van der Smagt P, Donoghue J P (2012, May) Reach and grasp by people with tetraplegia using a neurally controlled robotic arm. *Nature*, 485(7398):372-5

[Kahn, 1999] Kahn, J. M., Katz, R. H., & Pister, K. S. (1999, August). Next century challenges: mobile networking for "Smart Dust". In *Proceedings of the 5th annual ACM/IEEE international conference on Mobile computing and networking* (pp. 271-278). ACM.

[Kiani, 2013a] Kiani, M., & Ghovanloo, M. (2013). A 20-Mb/s pulse harmonic modulation transceiver for wideband near-field data transmission. *Circuits and Systems II: Express Briefs, IEEE Transactions on*, 60(7), 382-386.

[Kiani, 2013b] Kiani, M., & Ghovanloo, M. (2013). A figure-of-merit for designing high-performance inductive power transmission links. *Industrial Electronics, IEEE Transactions on*, 60(11), 5292-5305.

[Kim, 2014] Kim, E. G., John, J. K., Tu, H., Zheng, Q., Loeb, J., Zhang, J., & Xu, Y. (2014). A hybrid silicon-parylene neural probe with locally flexible regions. *Sensors and Actuators B: Chemical*, 195, 416-422.

[Jow, 2010] Jow, U. M., & Ghovanloo, M. (2010). Optimization of data coils in a multiband wireless link for neuroprosthetic implantable devices. *Biomedical Circuits and Systems, IEEE Transactions on*, 4(5), 301-310.

[Lee, 2013] Lee, Y., Bang, S., Lee, I., Kim, Y., Kim, G., Ghaed, M. H., . . . & Blaauw, D. (2013). A Modular 1 mm Die-Stacked Sensing Platform With Low Power I C Inter-Die Communication and Multi-Modal Energy Harvesting. *Solid-State Circuits, IEEE Journal of*, 48(1), 229-243.

[Liu, 2014] Liu, T., Bihr, U., Anders, J., and Ortmanns, M. (2014). Liu, T., Bihr, U., Anders, J., & Ortmanns, M. (2014, June). Performance evaluation of a low power optical wireless link for biomedical data transfer. In *Circuits and Systems (ISCAS), 2014 IEEE International Symposium on* (pp. 870-873). IEEE.

[Lopez, 2013] Lopez, C. M., Andrei, A., Mitra, S., Welkenhuysen, M., Eberle, W., Bartic, C., . . . & Gielen, G. G. (2014). An implantable 455-active-electrode 52-channel CMOS neural probe. *Solid-State Circuits, IEEE Journal of*, 49(1), 248-261.

[Motoyoshi, 2009] Motoyoshi, M. (2009). Through-silicon via (TSV). *Proceedings of the IEEE*, 97(1), 43-48.

[Najafi, 1985] Najafi, K., Wise, K. D., & Mochizuki, T. (1985). A high-yield IC-compatible multichannel recording array. *Electron Devices, IEEE Transactions on*, 32(7), 1206-1211.

[Parker, 2010] Parker, J. L. (2009). U.S. patent application Ser. No. 12/549,786.

[Polikov, 2005] Polikov, V. S., Tresco, P. A., & Reichert, W. M. (2005). Response of brain tissue to chronically implanted neural electrodes. *Journal of neuroscience methods*, 148(1), 1-18.

[Quiroga, 2004] Quiroga, R. Q., Nadasdy, Z., & Ben-Shaul, Y. (2004). Unsupervised spike detection and sorting with wavelets and superparamagnetic clustering. *Neural computation*, 16(8), 1661-1687.

[Saeidi, 2013] Saeidi, N., Schuettler, M., Demosthenous, A., & Donaldson, N. (2013). Technology for integrated circuit micropackages for neural interfaces, based on gold-silicon wafer bonding. *Journal of Micromechanics and Microengineering*, 23(7), 075021.

[Seo, 2014] Seo, D., Carmena, J. M., Rabaey, J. M., Maharbiz, M. M., & Alon, E. (2015). Model validation of untethered, ultrasonic neural dust motes for cortical recording. *Journal of neuroscience methods*, 244, 114-122.

[Sohal, 2014] Sohal, H. S., Jackson, A., Jackson, R., Clowry, G. J., Vassilevski, K., O'Neill, A., & Baker, S. N. (2015). The sinusoidal probe: a new approach to improve electrode longevity. The chronic challenge-new vistas on long-term multisite contacts to the central nervous system.

[Stevenson and Kording, 2011] Stevenson, I. H., & Kording, K. P. (2011). How advances in neural recording affect data analysis. *Nature neuroscience*, 14(2), 139-142.

[Todorova, 2014] Todorova, S., Sadtler, P., Batista, A., Chase, S., & Ventura, V. (2014). To sort or not to sort: the impact of spike-sorting on neural decoding performance. *Journal of neural engineering*, 11(5), 056005.

[Velliste, 2008] Velliste, M., Perel, S., Spalding, M. C., Whitford, A. S., & Schwartz, A. B. (2008). Cortical control of a prosthetic arm for self-feeding. *Nature*, 453 (7198), 1098-1101.

[Viventi, 2011] Viventi, J., Kim, D. H., Vigeland, L., Frechette, E. S., Blanco, J. A., Kim, Y. S., . . . & Wulsin, D. F. (2011). Flexible, foldable, actively multiplexed, high-density electrode array for mapping brain activity in vivo. *Nature neuroscience*, 14(12), 1599-1605.

[Williams, 2015] Williams, I., Luan, S., Jackson, A., & Constandinou, T. G. (2015). Live demonstration: A scalable 32-channel neural recording and real-time FPGA based spike sorting system. In *Biomedical Circuits and Systems Conference (BioCAS), 2015 IEEE* (pp. 1-5). IEEE.

The invention claimed is:

1. A neural interface arrangement comprising:
a plurality of probes for subdural implantation into or onto a human brain, each probe including at least one sensing electrode, a coil for receiving power via inductive coupling, signal processing circuitry coupled to the sensing electrode(s), and a wireless transmitter for wirelessly transmitting data-carrying signals arising from the sensing electrode(s);
a set of coils for implantation above the dura, beneath the skull, the set of coils being for inductively coupling with the coil of each of the plurality of probes, for transmitting power to the probes, wherein the set of coils is embedded within a device of unitary form; and
a primary coil connected to the set of coils, the primary coil being for inductively coupling with an external transmitter device for receiving power from the external transmitter device;
wherein, in use, the primary coil is operable to receive power from the external transmitter device by inductive coupling and to cause the set of coils to transmit power to the plurality of probes by inductive coupling; and
wherein, in use, the plurality of probes are operable to wirelessly transmit data-carrying signals arising from the sensing electrodes.

2. The neural interface arrangement according to claim 1, wherein at least some of the probes include a plurality of discrete independent sensing electrodes.

3. The neural interface arrangement according to claim 2, wherein at least some of the probes are of drawing-pin-like form, having a head and a rigid shank;
wherein the plurality of sensing electrodes are located at different depth positions along the shank.

4. The neural interface arrangement according to claim 2, wherein at least some of the probes are of drawing-pin-like form, having a head and a non-rigid shank, the shank being made up of a plurality of insulated wires, each wire being connected to a respective electrode;
wherein the plurality of sensing electrodes are located at different depth positions along the shank.

5. The neural interface arrangement according to claim 1, wherein at least some of the probes are without a shank, for surface recording, the sensing electrode(s) being planar electrode(s).

6. The neural interface arrangement according to claim 1, wherein, with each of the plurality of probes, the or each electrode is configured to sense the local electric field potential on or in the brain.

7. The neural interface arrangement according to claim 1, wherein each of the plurality of probes further includes a reference electrode.

8. The neural interface arrangement according to claim 1, wherein, in each of the plurality of probes, the signal processing circuitry is in the form of a complementary metal-oxide semiconductor system on a chip; and
the signal processing circuitry includes a power management module and a communication module;
wherein the power management module includes rectification circuitry and regulation circuitry;
wherein the communication module includes downlink circuitry and uplink circuitry;
wherein the downlink circuitry is connected to configuration and control circuitry, for configuring and controlling the operation of the probe; and
wherein the uplink circuitry is connected to processing and encoding circuitry, for processing and encoding signals arising from the probe's electrode(s).

9. The neural interface arrangement according to claim 1, wherein, in the signal processing circuitry of each of the plurality of probes, the output of the or each sensing electrode is supplied to a respective low noise amplifier;
wherein the output of a reference electrode is also supplied to the or each low noise amplifier, such that the or each low noise amplifier subtracts the reference electrode signal from the respective sensing electrode signal;
wherein the output of each low noise amplifier is provided to a multiplexer and buffer; and
wherein the output of the multiplexer and buffer is provided to an analogue-to-digital converter, the output of which is then provided to the processing and encoding circuitry.

10. The neural interface arrangement according to claim 1, wherein, in each of the plurality of probes, the electrode(s) are coupled to the signal processing circuitry by means of one or more through-silicon-vias, or by means of conductors that are tunnelled within inter metal dielectrics, or by means of an interposer layer;
wherein, in each of the plurality of probes, the signal processing circuitry is provided within micropackaging;
wherein each of the plurality of probes is passivated in a protective insulator;
wherein each of the plurality of probes is encapsulated in a biocompatible coating; and
wherein, in each of the plurality of probes, the coil comprises a millimetre-scale coil.

11. The neural interface arrangement according to claim 1, wherein, in each of the plurality of probes, the electrode(s) are spring-biased into an extended position, the electrode(s) being held in a retracted position prior to implantation.

12. The neural interface arrangement according to claim 1, wherein, in the set of coils, the coils overlap with each other;
wherein, in the set of coils, the coils are millimetre-scale coils; and
wherein the device of unitary form, in which the set of coils is embedded, comprises a sheet.

13. The neural interface arrangement according to claim 1, further comprising a multiplexing chip connected between the set of coils and the primary coil;
wherein each coil in the set is independently connected to the multiplexing chip.

14. The neural interface arrangement according to claim 13, wherein the set of coils, the multiplexing chip and the primary coil are all comprised within the device of unitary form;
wherein the device of unitary form is coated in a flexible encapsulant.

15. The neural interface arrangement according to claim 1,
wherein the external transmitter device is a transceiver device;
wherein, for each probe, the wireless transmitter comprises the probe's coil, or a second coil, with which each probe is operable to transmit data-carrying signals arising from the sensing electrode(s) to the set of coils by inductive coupling; and
wherein the primary coil is operable to transmit data-carrying signals to the external transceiver device by inductive coupling.

16. The neural interface arrangement according to claim 1, additionally comprising an external receiver/transceiver device, and wherein, for each probe, the wireless transmitter is operable to transmit data-carrying signals directly to the external receiver/transceiver device.

17. The neural interface arrangement according to claim 16;
wherein the neural interface arrangement is configured to transmit data from the sensing electrodes to the external receiver/transceiver device at a rate of the order of ~1 Mbps; and
wherein the coupling between the external receiver/transceiver device and the primary coil uses an NFC link.

18. The neural interface arrangement according to claim 17, wherein the external receiver/transceiver device is coupled to a unit configured to process the data arising from the implanted probes and to effect control of a connected device based on said data.

19. A method of controlling a connected device using a system comprising a neural interface arrangement, and an external transmitter device and an external receiver device, or an external transceiver device, said method comprising:
subdurally implanting a plurality of probes subdurally implanted into or onto a human brain, each probe including at least one sensing electrode, a coil that receives power via inductive coupling, signal processing circuitry coupled to the sensing electrode(s), and a wireless transmitter that wirelessly transmits data-carrying signals arising from the sensing electrode(s);

implanting a set of coils above the dura, beneath the skull, the set of coils inductively coupling with the coil of each of the plurality of probes, wherein the set of coils is embedded within a device of unitary form;

connecting a primary coil to the set of coils, the primary coil inductively coupling with the external transmitter device, so that the primary coil receives power from the external transmitter device by inductive coupling and causes the set of coils to transmit power to the plurality of probes by inductive coupling, thereby causing the plurality of probes to wirelessly transmit data-carrying signals arising from the sensing electrodes to the external receiver/transceiver device; and coupling the receiver/transceiver device to a unit configured to process the data arising from the implanted probes and to effect control of a connected device based on said data.

20. A surgical method of installing a neural interface arrangement into a patient, the neural interface arrangement comprising:

a plurality of probes for subdural implantation into or onto a human brain, each probe including at least one sensing electrode, a coil for receiving power via inductive coupling, signal processing circuitry coupled to the sensing electrode(s), and a wireless transmitter for wirelessly transmitting data-carrying signals arising from the sensing electrode(s);

a set of coils for implantation above the dura, beneath the skull, the set of coils being for inductively coupling with the coil of each of the plurality of probes, for transmitting power to the probes, wherein the set of coils is embedded within a device of unitary form; and a primary coil connected to the set of coils, the primary coil being for inductively coupling with an external transmitter device, for receiving power from the external transmitter device;

wherein, in use, the primary coil is operable to receive power from the external transmitter device by inductive coupling and to cause the set of coils to transmit power to the plurality of probes by inductive coupling; and wherein, in use, the plurality of probes are operable to wirelessly transmit data-carrying signals arising from the sensing electrodes;

the surgical method comprising:

removing a section of the patient's skull, and associated skin;

opening the dura beneath the removed skull;

implanting the plurality of probes into or onto the patient's brain;

sealing the dura over the implanted probes; and re-fitting the removed skull section or an artificial replacement therefor, with the set of coils embedded within the device of unitary form having been installed beneath the skull, above the dura, and the primary coil having been installed beneath the skin, above the skull, or elsewhere on the patient's body.

\* \* \* \* \*